(12) United States Patent
Roein Peikar et al.

(10) Patent No.: US 12,295,808 B2
(45) Date of Patent: May 13, 2025

(54) DENTAL APPLIANCES AND ASSOCIATED METHODS OF MANUFACTURING

(71) Applicant: Brius Technologies, Inc., Addison, TX (US)

(72) Inventors: Seyed Mehdi Roein Peikar, Addison, TX (US); James Sylvester Wratten, Jr., Waterville, NY (US)

(73) Assignee: Brius Technologies, Inc., Addison, TX (US)

( * ) Notice: Subject to any disclaimer, the term of this patent is extended or adjusted under 35 U.S.C. 154(b) by 105 days.

(21) Appl. No.: 15/929,442

(22) Filed: May 2, 2020

(65) Prior Publication Data

US 2020/0345455 A1 Nov. 5, 2020

Related U.S. Application Data

(60) Provisional application No. 62/842,391, filed on May 2, 2019.

(51) Int. Cl.
*A61C 7/20* (2006.01)
*A61C 7/00* (2006.01)
(Continued)

(52) U.S. Cl.
CPC .............. *A61C 7/146* (2013.01); *A61C 7/002* (2013.01); *A61C 7/145* (2013.01); *A61C 7/20* (2013.01); *G16H 20/40* (2018.01)

(58) Field of Classification Search
CPC .. A61C 7/002; A61C 7/20; A61C 7/22; A61C 7/10; A61C 9/0046; A61C 7/145;
(Continued)

(56) References Cited

U.S. PATENT DOCUMENTS

| 659,577 A | 10/1900 | Cederstrom |
| 1,292,702 A | 1/1919 | Canning |

(Continued)

FOREIGN PATENT DOCUMENTS

| AU | 2016367144 B2 | 10/2021 |
| AU | 2021290322 A1 | 2/2022 |

(Continued)

OTHER PUBLICATIONS

Extended European Search Report dated Jul. 24, 2019, from Application No. 16873680.9.

(Continued)

*Primary Examiner* — Heidi M Eide
(74) *Attorney, Agent, or Firm* — Fortem IP LLP

(57) ABSTRACT

Orthodontic appliances and methods of manufacturing are disclosed. Manufacturing an appliance can include obtaining position data corresponding to an original tooth arrangement (OTA) of a patient's teeth, obtaining data corresponding to a desired final tooth arrangement (FTA) of the patient's teeth, and determining displacements between the OTA data and the FTA data. Based on the determined displacements, a configuration of an orthodontic appliance is determined. The appliance includes an anchor configured to be positioned adjacent the patient's teeth, and a plurality of arms each extending away from and coupled to the anchor, the arms configured to be secured to the patient's teeth. When the appliance is installed, the arms urge individual teeth from the OTA toward the FTA.

20 Claims, 16 Drawing Sheets

(51) Int. Cl.
   *A61C 7/14*      (2006.01)
   *G16H 20/40*    (2018.01)
(58) Field of Classification Search
   CPC ..... B29C 64/00; B29C 33/3835; B33Y 80/00;
   B33Y 30/00
   See application file for complete search history.

(56) References Cited

U.S. PATENT DOCUMENTS

| | | |
|---|---|---|
| 1,369,665 A | 2/1921 | Johnson |
| 2,259,160 A | 10/1941 | Glaser |
| 2,266,860 A | 12/1941 | Griesinger |
| 2,305,916 A | 12/1942 | Atkinson |
| 3,235,965 A | 2/1966 | Muir |
| 3,256,602 A | 6/1966 | Broussard et al. |
| 3,262,207 A | 7/1966 | Kesling |
| 3,416,228 A | 12/1968 | Grimmett |
| 3,421,221 A | 1/1969 | Silverman et al. |
| 3,464,112 A | 9/1969 | Silverman et al. |
| 3,464,113 A | 9/1969 | Silverman et al. |
| 3,505,736 A | 4/1970 | Brader et al. |
| 3,510,340 A | 5/1970 | Blake et al. |
| 3,593,421 A | 7/1971 | Brader |
| 3,618,214 A | 11/1971 | Armstrong |
| 3,738,005 A | 6/1973 | Cohen et al. |
| 3,762,050 A | 10/1973 | Dal |
| 3,792,529 A | 2/1974 | Goshgarian |
| 3,815,237 A | 6/1974 | Wallshein |
| 3,936,938 A | 2/1976 | Northcutt |
| 4,037,324 A | 7/1977 | Andreasen |
| 4,197,643 A | 4/1980 | Burstone et al. |
| 4,272,241 A * | 6/1981 | Crisalli .............. A61C 13/2255 264/17 |
| 4,354,834 A | 10/1982 | Wilson |
| 4,360,342 A | 11/1982 | Salvo |
| 4,433,960 A | 2/1984 | Garito et al. |
| 4,468,196 A | 8/1984 | Keller |
| 4,479,779 A | 10/1984 | Wool |
| 4,516,938 A | 5/1985 | Hall |
| 4,533,320 A | 8/1985 | Piekarsky |
| 4,571,179 A | 2/1986 | Balenseifen |
| 4,731,018 A | 3/1988 | Adell |
| 4,815,968 A | 3/1989 | Keller |
| 4,932,866 A | 6/1990 | Guis |
| 4,976,614 A | 12/1990 | Tepper |
| 5,022,855 A | 6/1991 | Jeckel |
| 5,120,218 A | 6/1992 | Hanson |
| 5,167,499 A | 12/1992 | Arndt et al. |
| 5,255,352 A | 10/1993 | Falk |
| 5,295,886 A * | 3/1994 | Wildman ................. A61C 7/12 433/20 |
| 5,310,340 A * | 5/1994 | Zedda ...................... A61C 7/00 433/18 |
| 5,312,247 A | 5/1994 | Sachdeva et al. |
| 5,380,197 A | 1/1995 | Hanson |
| 5,429,501 A | 7/1995 | Farzin-Nia et al. |
| 5,431,562 A | 7/1995 | Andreiko et al. |
| 5,435,721 A | 7/1995 | Vogt |
| 5,536,169 A | 7/1996 | Yousefian |
| 5,580,243 A | 12/1996 | Bloore |
| 5,624,258 A | 4/1997 | Wool |
| 5,645,423 A | 7/1997 | Collins |
| 5,791,897 A | 8/1998 | Wildman |
| 5,829,980 A | 11/1998 | Sheridan et al. |
| 5,975,893 A | 11/1999 | Chishti et al. |
| 6,053,730 A | 4/2000 | Cleary |
| 6,086,364 A | 7/2000 | Brunson |
| 6,174,163 B1 | 1/2001 | Hiro |
| 6,190,166 B1 | 2/2001 | Sasakura |
| 6,220,856 B1 | 4/2001 | Carano et al. |
| 6,254,384 B1 | 7/2001 | Rosenberg |
| 6,302,688 B1 | 10/2001 | Jordan et al. |
| 6,406,292 B1 | 6/2002 | Chishti et al. |
| 6,471,511 B1 | 10/2002 | Chishti et al. |
| 6,582,226 B2 | 6/2003 | Jordan et al. |
| 6,685,469 B2 | 2/2004 | Chishti et al. |
| 6,688,886 B2 | 2/2004 | Hughes et al. |
| 6,732,558 B2 | 5/2004 | Butscher et al. |
| 6,739,870 B2 | 5/2004 | Lai et al. |
| 6,755,064 B2 | 6/2004 | Butscher et al. |
| 6,860,132 B2 | 3/2005 | Butscher et al. |
| 6,884,067 B2 | 4/2005 | Tuneberg |
| 6,908,306 B2 | 6/2005 | Bowman et al. |
| 6,928,733 B2 * | 8/2005 | Rubbert .................. A61C 7/20 29/407.04 |
| 6,935,858 B2 | 8/2005 | Cleary |
| 6,984,127 B2 | 1/2006 | Lai |
| 7,020,963 B2 | 4/2006 | Cleary et al. |
| 7,056,115 B2 | 6/2006 | Phan et al. |
| 7,063,531 B2 | 6/2006 | Maijer et al. |
| 7,074,039 B2 | 7/2006 | Kopelman et al. |
| 7,076,980 B2 | 7/2006 | Butscher et al. |
| 7,077,647 B2 | 7/2006 | Choi et al. |
| 7,112,065 B2 | 9/2006 | Kopelman et al. |
| 7,131,836 B1 | 11/2006 | Kesling |
| 7,156,661 B2 | 1/2007 | Choi et al. |
| 7,210,929 B2 | 5/2007 | Raby et al. |
| 7,234,934 B2 | 6/2007 | Rosenberg |
| 7,240,528 B2 | 7/2007 | Weise et al. |
| 7,283,891 B2 | 10/2007 | Butscher et al. |
| 7,291,011 B2 | 11/2007 | Stark et al. |
| 7,335,021 B2 | 2/2008 | Nikodem |
| 7,347,688 B2 | 3/2008 | Kopelman et al. |
| 7,354,268 B2 | 4/2008 | Raby et al. |
| 7,357,634 B2 | 4/2008 | Knopp |
| 7,377,778 B2 | 5/2008 | Chishti et al. |
| 7,416,407 B2 | 8/2008 | Cronauer |
| 7,433,810 B2 | 10/2008 | Pavloskaia et al. |
| 7,556,496 B2 | 7/2009 | Cinader et al. |
| 7,578,673 B2 | 8/2009 | Wen et al. |
| 7,580,846 B2 | 8/2009 | Chishti et al. |
| 7,600,999 B2 | 10/2009 | Knopp |
| 7,613,527 B2 | 11/2009 | Raby et al. |
| 7,641,473 B2 | 1/2010 | Sporbert et al. |
| 7,658,610 B2 | 2/2010 | Knopp |
| 7,708,557 B2 | 5/2010 | Rubbert |
| 7,726,968 B2 | 6/2010 | Raby et al. |
| 7,785,102 B2 | 8/2010 | Papadopoulos |
| 7,837,466 B2 | 11/2010 | Griffith et al. |
| 7,837,469 B2 | 11/2010 | Chishti et al. |
| 7,844,356 B2 | 11/2010 | Matov et al. |
| 7,869,983 B2 | 1/2011 | Raby et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,940,258 B2 | 5/2011 | Stark et al. |
| 7,987,099 B2 | 7/2011 | Kuo et al. |
| 7,993,133 B2 | 8/2011 | Cinader et al. |
| RE42,815 E | 10/2011 | Rubbert et al. |
| 8,075,306 B2 | 12/2011 | Kitching et al. |
| 8,092,215 B2 | 1/2012 | Stone-Collonge et al. |
| 8,131,393 B2 | 3/2012 | Matov et al. |
| 8,192,196 B2 | 6/2012 | Singh |
| 8,194,067 B2 | 6/2012 | Raby et al. |
| 8,266,940 B2 | 9/2012 | Riemeier et al. |
| 8,292,617 B2 | 10/2012 | Brandt et al. |
| 8,308,478 B2 | 11/2012 | Primus et al. |
| 8,326,647 B2 | 12/2012 | Chishti et al. |
| 8,356,993 B1 | 1/2013 | Marston |
| 8,382,917 B2 | 2/2013 | Johnson |
| 8,401,686 B2 | 3/2013 | Moss et al. |
| 8,417,366 B2 | 4/2013 | Getto et al. |
| 8,439,673 B2 | 5/2013 | Korytov et al. |
| 8,496,473 B2 | 7/2013 | Phan et al. |
| 8,517,726 B2 | 8/2013 | Kakavand et al. |
| 8,517,727 B2 | 8/2013 | Raby et al. |
| 8,529,253 B2 | 9/2013 | Jasper |
| 8,545,221 B2 | 10/2013 | Stone-Collonge et al. |
| 8,550,814 B1 | 10/2013 | Collins |
| 8,562,338 B2 | 10/2013 | Kitching et al. |
| 8,573,972 B2 | 11/2013 | Matov et al. |
| 8,591,225 B2 | 11/2013 | Wu et al. |

(56) References Cited

U.S. PATENT DOCUMENTS

| | | | |
|---|---|---|---|
| RE44,668 E | 12/2013 | Rubbert et al. | |
| 8,606,598 B2 | 12/2013 | Chishti et al. | |
| 8,636,510 B2 | 1/2014 | Kitching et al. | |
| 8,651,859 B2 | 2/2014 | Chishti et al. | |
| 8,685,184 B2 | 4/2014 | Johnson et al. | |
| 8,734,149 B2 | 5/2014 | Phan et al. | |
| 8,801,633 B2 | 8/2014 | Fox et al. | |
| 8,827,697 B2 * | 9/2014 | Cinader, Jr. | A61C 7/08 433/6 |
| 8,899,978 B2 | 12/2014 | Kitching et al. | |
| 8,932,054 B1 | 1/2015 | Rosenberg | |
| 8,944,812 B2 | 2/2015 | Kuo | |
| 8,992,215 B2 | 3/2015 | Chapoulaud et al. | |
| 9,017,070 B2 | 4/2015 | Parker | |
| 9,017,072 B2 | 4/2015 | Kitching et al. | |
| 9,060,829 B2 | 6/2015 | Sterental et al. | |
| 9,061,124 B2 | 6/2015 | Fox et al. | |
| 9,127,338 B2 | 9/2015 | Johnson | |
| 9,144,472 B2 | 9/2015 | Isaacson et al. | |
| 9,149,344 B2 | 10/2015 | Gautam | |
| 9,161,823 B2 | 10/2015 | Morton et al. | |
| 9,168,113 B2 | 10/2015 | Wu et al. | |
| 9,204,942 B2 | 12/2015 | Phan et al. | |
| 9,220,580 B2 | 12/2015 | Borovinskih et al. | |
| 9,271,809 B2 | 3/2016 | Korytov et al. | |
| 9,320,575 B2 | 4/2016 | Chishti et al. | |
| 9,326,831 B2 | 5/2016 | Cheang | |
| 9,328,406 B2 | 5/2016 | Johnson et al. | |
| 9,364,297 B2 | 6/2016 | Kitching et al. | |
| 9,375,300 B2 | 6/2016 | Matov et al. | |
| 9,427,291 B2 | 8/2016 | Khoshnevis et al. | |
| 9,433,479 B2 | 9/2016 | Phan et al. | |
| 9,492,245 B2 | 11/2016 | Sherwood et al. | |
| 9,498,302 B1 | 11/2016 | Patel | |
| 9,504,544 B2 | 11/2016 | Conley et al. | |
| 9,532,854 B2 | 1/2017 | Cinader et al. | |
| 9,554,875 B2 | 1/2017 | Gualano | |
| 9,566,132 B2 | 2/2017 | Stone-Collonge et al. | |
| 9,566,133 B2 | 2/2017 | Vu | |
| 9,572,971 B2 | 2/2017 | Su | |
| 9,610,628 B2 | 4/2017 | Riemeier et al. | |
| 9,642,678 B2 | 5/2017 | Kuo | |
| 9,707,054 B2 | 7/2017 | Chishti et al. | |
| 9,757,211 B2 | 9/2017 | Ward | |
| 9,770,217 B2 | 9/2017 | Sandholm et al. | |
| 9,844,420 B2 | 12/2017 | Cheang | |
| 9,883,924 B2 | 2/2018 | Rudman | |
| 9,925,019 B2 | 3/2018 | Cinader et al. | |
| 9,925,025 B2 | 3/2018 | Conley et al. | |
| 9,937,018 B2 | 4/2018 | Martz et al. | |
| 10,022,204 B2 | 7/2018 | Cheang | |
| 10,052,174 B2 | 8/2018 | Kitching et al. | |
| 10,154,890 B2 | 12/2018 | Johnson et al. | |
| 10,226,312 B2 | 3/2019 | Khoshnevis et al. | |
| 10,231,801 B2 | 3/2019 | Korytov et al. | |
| 10,248,883 B2 | 4/2019 | Borovinskih et al. | |
| 10,278,791 B2 | 5/2019 | Schumacher | |
| 10,342,638 B2 | 7/2019 | Kitching et al. | |
| 10,363,116 B2 | 7/2019 | Boronkay | |
| 10,368,960 B2 | 8/2019 | Wu et al. | |
| 10,383,707 B2 | 8/2019 | Roein Peikar et al. | |
| 10,413,385 B2 | 9/2019 | Sherwood et al. | |
| 10,413,386 B2 | 9/2019 | Moon et al. | |
| 10,478,271 B2 | 11/2019 | Patel | |
| 10,512,524 B2 | 12/2019 | Kuo | |
| 10,517,696 B2 | 12/2019 | Kitching et al. | |
| 10,548,690 B2 | 2/2020 | Wen | |
| 10,610,332 B2 | 4/2020 | Wu et al. | |
| 10,624,716 B2 | 4/2020 | Kitching et al. | |
| 10,729,516 B2 | 8/2020 | Hung | |
| 10,758,321 B2 | 9/2020 | Stone-Collonge et al. | |
| 10,792,127 B2 | 10/2020 | Kopelman et al. | |
| 10,799,321 B2 | 10/2020 | Salah et al. | |
| 10,813,721 B2 | 10/2020 | Sterental et al. | |
| 10,905,527 B2 | 2/2021 | Roein Peikar et al. | |
| 10,980,614 B2 | 4/2021 | Roein Peikar et al. | |
| 10,993,785 B2 | 5/2021 | Roein Peikar et al. | |
| 11,000,350 B2 | 5/2021 | Kuo | |
| 11,024,431 B2 | 6/2021 | Stone-Collonge et al. | |
| 11,042,774 B2 | 6/2021 | Borovinskih et al. | |
| 11,058,518 B2 | 7/2021 | Roein Peikar et al. | |
| 11,058,520 B2 * | 7/2021 | Khoshnevis | A61C 7/28 |
| 11,071,608 B2 | 7/2021 | Derakhshan et al. | |
| 11,096,763 B2 | 8/2021 | Akopov et al. | |
| 11,317,994 B2 | 5/2022 | Roein Peikar et al. | |
| 11,317,995 B2 | 5/2022 | Roein Peikar et al. | |
| 11,324,572 B2 | 5/2022 | Roein Peikar et al. | |
| 11,490,995 B2 | 11/2022 | Wratten et al. | |
| 11,504,212 B2 | 11/2022 | Wratten et al. | |
| 11,529,216 B2 | 12/2022 | Roein Peikar et al. | |
| 11,864,974 B2 | 1/2024 | Roein Peikar et al. | |
| 12,144,700 B2 | 11/2024 | Wratten et al. | |
| 2001/0002310 A1 * | 5/2001 | Chishti | A61C 7/08 345/20 |
| 2002/0064746 A1 * | 5/2002 | Muhammad | A61C 7/00 433/24 |
| 2003/0003416 A1 * | 1/2003 | Chishti | A61C 7/08 433/24 |
| 2003/0075186 A1 | 4/2003 | Florman | |
| 2003/0091952 A1 | 5/2003 | Bowman et al. | |
| 2003/0096210 A1 | 5/2003 | Rubbert et al. | |
| 2003/0118967 A1 | 6/2003 | Tepper | |
| 2003/0157455 A1 | 8/2003 | Teramoto | |
| 2004/0009449 A1 | 1/2004 | Mah et al. | |
| 2004/0048222 A1 | 3/2004 | Forster et al. | |
| 2004/0067463 A1 | 4/2004 | Rosenberg | |
| 2004/0072120 A1 * | 4/2004 | Lauren | A61C 7/20 433/20 |
| 2004/0083611 A1 | 5/2004 | Rubbert et al. | |
| 2004/0131989 A1 | 7/2004 | Dellinger | |
| 2004/0209218 A1 | 10/2004 | Chishti et al. | |
| 2004/0214126 A1 | 10/2004 | Forster et al. | |
| 2005/0048432 A1 | 3/2005 | Choi et al. | |
| 2005/0048433 A1 | 3/2005 | Hilliard | |
| 2005/0130094 A1 | 6/2005 | Graham | |
| 2005/0227196 A1 | 10/2005 | Von | |
| 2005/0239012 A1 | 10/2005 | Bathen et al. | |
| 2005/0244780 A1 | 11/2005 | Abels et al. | |
| 2006/0073436 A1 | 4/2006 | Raby et al. | |
| 2006/0093984 A1 | 5/2006 | Rosenberg | |
| 2006/0099544 A1 | 5/2006 | Lai et al. | |
| 2006/0099545 A1 | 5/2006 | Lai et al. | |
| 2006/0234179 A1 | 10/2006 | Wen et al. | |
| 2006/0240374 A1 | 10/2006 | Wen | |
| 2007/0134625 A1 * | 6/2007 | Leu | A61C 8/0048 433/215 |
| 2007/0259301 A1 | 11/2007 | Hagelganz et al. | |
| 2007/0264605 A1 | 11/2007 | Belfor et al. | |
| 2008/0020339 A1 | 1/2008 | Papadopoulos | |
| 2008/0032258 A1 | 2/2008 | Kyung et al. | |
| 2008/0057460 A1 | 3/2008 | Hicks | |
| 2008/0254403 A1 * | 10/2008 | Hilliard | A61C 7/20 433/24 |
| 2008/0311535 A1 | 12/2008 | Andreiko | |
| 2009/0098500 A1 | 4/2009 | Diaz | |
| 2009/0311645 A1 * | 12/2009 | Matty | A61C 19/066 433/6 |
| 2010/0068671 A1 | 3/2010 | Kakavand et al. | |
| 2010/0075268 A1 | 3/2010 | Duran | |
| 2010/0092905 A1 * | 4/2010 | Martin | A61C 7/00 433/18 |
| 2010/0173256 A1 | 7/2010 | Rodriguez et al. | |
| 2010/0279245 A1 | 11/2010 | Navarro | |
| 2011/0027743 A1 | 2/2011 | Cinader et al. | |
| 2011/0083767 A1 * | 4/2011 | Johnson | C22F 1/00 140/71 R |
| 2011/0269095 A1 | 11/2011 | Singh | |
| 2011/0270583 A1 * | 11/2011 | Getto | A61C 7/20 703/1 |
| 2012/0015316 A1 | 1/2012 | Sachdeva et al. | |
| 2012/0048432 A1 | 3/2012 | Johnson et al. | |
| 2012/0123577 A1 | 5/2012 | Chapoulaud et al. | |
| 2012/0225398 A1 | 9/2012 | Fallah | |

(56) References Cited

U.S. PATENT DOCUMENTS

| | | |
|---|---|---|
| 2012/0322019 A1 | 12/2012 | Lewis |
| 2013/0252195 A1 | 9/2013 | Popat |
| 2014/0120491 A1 | 5/2014 | Khoshnevis et al. |
| 2014/0154637 A1* | 6/2014 | Hansen .................. A61C 7/002 433/20 |
| 2014/0170585 A1 | 6/2014 | Parker |
| 2014/0234794 A1* | 8/2014 | Vu .......................... A61C 7/282 433/20 |
| 2014/0302448 A1 | 10/2014 | Cassalia |
| 2014/0356799 A1 | 12/2014 | Cinader et al. |
| 2015/0157421 A1 | 6/2015 | Martz et al. |
| 2015/0245888 A1 | 9/2015 | Hasegawa |
| 2015/0257856 A1 | 9/2015 | Martz et al. |
| 2016/0058527 A1 | 3/2016 | Schumacher |
| 2016/0095670 A1* | 4/2016 | Witte ...................... A61C 7/002 433/24 |
| 2016/0095672 A1 | 4/2016 | Izadi |
| 2016/0106520 A1 | 4/2016 | Borovinskih et al. |
| 2016/0135925 A1 | 5/2016 | Mason et al. |
| 2016/0135926 A1 | 5/2016 | Djamchidi |
| 2016/0278882 A1 | 9/2016 | Kitching et al. |
| 2016/0302890 A1 | 10/2016 | Hamilton |
| 2016/0324601 A1 | 11/2016 | Phan et al. |
| 2016/0346064 A1 | 12/2016 | Schulhof et al. |
| 2016/0367340 A1 | 12/2016 | Ward |
| 2017/0007365 A1 | 1/2017 | Kopelman et al. |
| 2017/0100215 A1* | 4/2017 | Khouri ................ A61C 8/0096 |
| 2017/0156823 A1* | 6/2017 | Roein Peikar ........... A61C 7/12 |
| 2017/0245963 A1 | 8/2017 | Hirsch |
| 2017/0296304 A1 | 10/2017 | Tong et al. |
| 2018/0014916 A1 | 1/2018 | Cinader et al. |
| 2018/0021108 A1 | 1/2018 | Cinader et al. |
| 2018/0049847 A1 | 2/2018 | Oda et al. |
| 2018/0071057 A1 | 3/2018 | Rudman |
| 2018/0116762 A1 | 5/2018 | Kopelman |
| 2018/0142377 A1 | 5/2018 | Gao et al. |
| 2018/0153651 A1 | 6/2018 | Tong et al. |
| 2018/0185125 A1 | 7/2018 | Salah et al. |
| 2018/0189434 A1 | 7/2018 | Zhou et al. |
| 2018/0221113 A1 | 8/2018 | Tong et al. |
| 2018/0303583 A1 | 10/2018 | Tong et al. |
| 2018/0311014 A1 | 11/2018 | Yousefian |
| 2018/0325629 A1 | 11/2018 | Cursio |
| 2018/0338564 A1 | 11/2018 | Oda et al. |
| 2018/0353265 A1 | 12/2018 | Paehl et al. |
| 2019/0015178 A1 | 1/2019 | Wiechmann |
| 2019/0069974 A1 | 3/2019 | Schumacher |
| 2019/0090985 A1 | 3/2019 | Jo |
| 2019/0090988 A1 | 3/2019 | Schumacher et al. |
| 2019/0321136 A1 | 10/2019 | Martz et al. |
| 2019/0321138 A1 | 10/2019 | Roein Peikar et al. |
| 2020/0022785 A1* | 1/2020 | Bear ....................... A61C 7/20 |
| 2020/0078140 A1 | 3/2020 | Roein Peikar et al. |
| 2020/0085540 A1 | 3/2020 | Roein Peikar et al. |
| 2020/0085541 A1 | 3/2020 | Roein Peikar et al. |
| 2020/0093569 A1 | 3/2020 | Kitching et al. |
| 2020/0100866 A1 | 4/2020 | Medvinskaya et al. |
| 2020/0107911 A1 | 4/2020 | Roein Peikar |
| 2020/0129272 A1 | 4/2020 | Roein Peikar et al. |
| 2020/0345460 A1* | 11/2020 | Roein Peikar .......... A61C 7/287 |
| 2020/0375699 A1 | 12/2020 | Roein Peikar et al. |
| 2020/0390524 A1 | 12/2020 | Roein Peikar et al. |
| 2021/0007830 A1 | 1/2021 | Roein Peikar et al. |
| 2021/0007832 A1 | 1/2021 | Roein Peikar et al. |
| 2021/0169616 A1 | 6/2021 | Jo |
| 2021/0177551 A1 | 6/2021 | Roein Peikar et al. |
| 2021/0186662 A1 | 6/2021 | Roein Peikar et al. |
| 2021/0353389 A1 | 11/2021 | Roein Peikar et al. |
| 2022/0015868 A1 | 1/2022 | Mason et al. |
| 2022/0023009 A1 | 1/2022 | Tong et al. |
| 2022/0054232 A1 | 2/2022 | Wen et al. |
| 2022/0133438 A1 | 5/2022 | Wratten et al. |
| 2022/0226076 A1 | 7/2022 | Roein Peikar et al. |
| 2022/0226077 A1 | 7/2022 | Roein Peikar et al. |
| 2022/0287804 A1 | 9/2022 | Oda |
| 2022/0304773 A1 | 9/2022 | Wratten et al. |
| 2022/0304774 A1 | 9/2022 | Wratten et al. |
| 2023/0138021 A1 | 5/2023 | Wratten et al. |
| 2023/0414327 A1 | 12/2023 | Roein Peikar et al. |

FOREIGN PATENT DOCUMENTS

| | | |
|---|---|---|
| CA | 2511247 C | 6/2009 |
| CN | 1845709 A | 10/2006 |
| CN | 201079455 Y | 7/2008 |
| CN | 101277658 A | 10/2008 |
| CN | 101351165 A | 1/2009 |
| CN | 102560303 A | 7/2012 |
| CN | 102711655 A | 10/2012 |
| CN | 103384504 A | 11/2013 |
| CN | 104146786 A | 11/2014 |
| CN | 104814808 A | 8/2015 |
| CN | 104887332 A | 9/2015 |
| CN | 105997273 A | 10/2016 |
| CN | 106491221 A | 3/2017 |
| CN | 207949917 U | 10/2018 |
| CN | 109069229 A | 12/2018 |
| CN | 114080197 A | 2/2022 |
| CN | 115916101 A | 4/2023 |
| DE | 102015009345 A1 | 1/2016 |
| EP | 0400932 A3 | 1/1991 |
| EP | 0551800 A1 | 7/1993 |
| EP | 1379193 B1 | 2/2007 |
| EP | 1301140 B1 | 11/2010 |
| EP | 3383309 A1 | 10/2018 |
| EP | 3962401 A1 | 3/2022 |
| GB | 974100 A | 11/1964 |
| GB | 2521046 A | 6/2015 |
| JP | H0634607 U | 5/1994 |
| JP | H08280711 A | 10/1996 |
| JP | 2002102256 A | 4/2002 |
| JP | 2003204973 A | 7/2003 |
| JP | 2003527131 A | 9/2003 |
| JP | 3636660 B2 | 1/2005 |
| JP | 2005110830 A | 4/2005 |
| JP | 2005177161 A | 7/2005 |
| JP | 2006000489 A | 1/2006 |
| JP | 2006246978 A | 9/2006 |
| JP | 2009504247 A | 2/2009 |
| JP | 2011517603 A | 6/2011 |
| JP | 2015527159 A | 9/2015 |
| JP | 2018536527 A | 12/2018 |
| KR | 1020150128917 A | 11/2015 |
| KR | 20180107481 A | 10/2018 |
| SU | 1502023 A1 | 8/1989 |
| WO | 9725010 A1 | 7/1997 |
| WO | 01/80761 A2 | 11/2001 |
| WO | 0219939 A1 | 3/2002 |
| WO | 2007021468 A2 | 2/2007 |
| WO | 2009126433 A2 | 10/2009 |
| WO | 2010146192 A1 | 12/2010 |
| WO | 2011103669 A1 | 9/2011 |
| WO | 2014088422 A1 | 6/2014 |
| WO | 2014140013 A1 | 9/2014 |
| WO | 2015032918 A1 | 3/2015 |
| WO | 2016149007 A1 | 9/2016 |
| WO | 2016149008 A1 | 9/2016 |
| WO | 2017007964 A1 | 1/2017 |
| WO | 2017100198 A1 | 6/2017 |
| WO | 2018215863 A1 | 11/2018 |
| WO | 2019043005 A1 | 3/2019 |
| WO | 2019064127 A1 | 4/2019 |
| WO | 2020069446 A1 | 4/2020 |
| WO | 2020223714 A1 | 11/2020 |
| WO | 2020223744 A1 | 11/2020 |
| WO | 2020223745 A1 | 11/2020 |
| WO | 2020223745 A9 | 11/2020 |
| WO | 2021225916 A2 | 11/2021 |
| WO | 2021225916 A3 | 11/2021 |
| WO | 2021226618 A1 | 11/2021 |

(56) References Cited

FOREIGN PATENT DOCUMENTS

| WO | 2021252675 A1 | 12/2021 |
|---|---|---|
| WO | 2022204711 A1 | 9/2022 |

OTHER PUBLICATIONS

International Report on Patentability dated Jun. 21, 2018, from Application No. PCT/US2016/065174.
International Search Report and Written Opinion dated Mar. 13, 2017, from related International Application No. PCT/US2016/065174.
Khosravi, Rooz , "Biomechanics in lingual orthodontics: What the future holds", Seminars in Orthodontics,vol. 24, No. 3, 2018, 363-371.
International Search Report and Written Opinion mailed Aug. 6, 2020, International Application No. PCT/US2020/031211, 28 pages.
International Search Report and Written Opinion mailed Aug. 26, 2020, International Application No. PCT/US20/70017, 12 pages.
International Search Report and Written Opinion mailed Oct. 8, 2020, International Application No. PCT/US20/70016, 18 pages.
International Search Report and Written Opinion mailed Jul. 19, 2021, International Application No. PCT/US2021/070469, 14 pages.
International Search Report and Written Opinion mailed Nov. 11, 2021, International Application No. PCT/US2021/030377, 24 pages.
Baron Pascal, et al., "Customized Brackets and the Straight Arch Technique Combined in One Appliance to Simplify Lingual Orthodontics", J. Dentofacial Anom Orthod, 2012, pp. 1-16.
Faber Zackary, "Incognito Customized Orthodontic Appliance: A Giant Leap Forward in Orthodontic Technology", Dentistry iQ, 2012, pp. 1-5.
Gracco Antonio, et al., "The Insignia System of Customized Orthodontics", JCO, Inc., 2011, pp. 442-451.
Kusy Robert, "Orthodontic Biomaterials: From the Past to the Present", The Angle Orthodontist, 2002, pp. 501-512.
Mankar Mugdha, et al., "Precision Multiloop (PM Design) with Space Closing Circles for Lingual Orhodontics", Journal of Indian Orthodontic Society, 2016, pp. S88-S93.
Miura Fujio, et al., "New Application of Superelastic NiTi Rectangular Wire", J. Clin. Orthod., 1990, pp. 544-548.
Raboud D.W., "Superelastic Response to NiTi Shape Memory Alloy Wires for Orthodontic Applications", Smart Materials and Stuctures, 2000, pp. 684-692.
Ribeiro Gerson Luiz Ulema, et al., "Multiloop Edgewise Archwire in the Treatment of a Patient with an Anterior Open Bite and a Long Face", American Journal of Orthodontics and Dentofacial Orthopedics, 2010, pp. 89-95.
Sanjay N., et al., "Space Closure with Loop Mechanics for Treatment of Bimaxillary Protrusion: A Case Report", Journal of International Oral Health, 2015, pp. 65-67.
Siatkowski Raymond, "Continuous Arch Wire Closing Loop Design, Optimization, and Verification. Part I", American Journal of Orthodontics and Dentofacial Orthopedics, 1997, pp. 393-408.
Teramoto Alberto, "Sentalloy the Story of Superelasticity", Materials Science, 2012, pp. 1-12.
Viecilli Amanda, et al., "The T-Loop in Details", Dental Press J. Orthod., 2018, pp. 108-117.
Werner Alison, "MEAW Therapy", Orthodontic Products, https://orthodonticproductsonline.com/clinical-tips/meaw-therapy/, 2012, pp. 1-7.
Wiechmann Dirk, et al., "Customized Brackets and Archwire for Lingual Orthodontic Treatment", American Journal of Orthodontics and Dentofacial Orthopedics, 2003, pp. 593-599.
Yang Won-Sik, et al., "A Study of the Regional Load Deflection Rate of Multiloop Edgewise Arch Wire", The Angle Orthodontist, 2001, pp. 103-109.
KR20180107481A (Yoon Sung Hee; Oh Yoon Joon) (Biocetec Co Ltd) Self ligation orthodontic bracket assembly, Oct. 2, 2018. [retrieved on May 26, 2022], Translation retrieved from: Espacenet (Year: 2018).
Churnjitapirom, P. , et al., "Effect of Heat Treatment on Mechanical Properties of General Purpose Stainless Steel Archwire", Advanced Materials Research (vol. 746); Dec. 31, 2013; 444-449; 1-39.

\* cited by examiner

DENTAL APPLIANCES AND ASSOCIATED METHODS OF MANUFACTURING

CROSS-REFERENCE TO RELATED APPLICATIONS

The present application claims priority to U.S. Provisional Application No. 62/842,391, filed May 2, 2019, which is hereby incorporated by reference in its entirety.

This application is also related to the following applications, each of which is hereby incorporated by reference in its entirety: U.S. Provisional Patent Application No. 62/956,290, filed Jan. 1, 2020; U.S. patent application Ser. No. 16/865,323, titled DENTAL APPLIANCES, SYSTEMS AND METHODS, filed May 2, 2020; International Patent Application No. PCT/US20/31211, titled DENTAL APPLIANCES, SYSTEMS AND METHODS, filed May 2, 2020; U.S. patent application Ser. No. 15/929,443, titled DENTAL APPLIANCES AND ASSOCIATED SYSTEMS AND METHODS OF USE, filed May 2, 2020; U.S. patent application Ser. No. 15/929,444, titled DENTAL APPLIANCES AND ASSOCIATED SYSTEMS AND METHODS OF USE, filed May 2, 2020; and International Application No. PCT/US20/70017, titled DENTAL APPLIANCES AND ASSOCIATED SYSTEMS AND METHODS OF USE, filed May 2, 2020.

TECHNICAL FIELD

The present technology relates to the field of orthodontics and, more particularly, to devices, systems, and methods for designing and manufacturing orthodontic appliances.

BACKGROUND

A common objective in orthodontics is to move a patient's teeth to positions where the teeth function optimally and aesthetically. To move the teeth, the orthodontist begins by obtaining multiple scans and/or impressions of the patient's teeth to determine a series of corrective paths between the initial positions of the teeth and the desired ending positions. The orthodontist then fits the patient to one of two main appliance types: braces or aligners.

Traditional braces consist of brackets and an archwire placed across a front side of the teeth, with elastic ties or ligature wires to secure the archwire to the brackets. In some cases self-ligating brackets may be used in lieu of ties or wires. The shape and stiffness of the archwire as well as the archwire-bracket interaction governs the forces applied to the teeth and thus the direction and degree of tooth movement. To exert a desired force on the teeth, the orthodontist often manually bends the archwire. The orthodontist monitors the patient's progress through regular appointments, during which the orthodontist visually assesses the progress of the treatment and makes manual adjustments to the archwire (such as new bends) and/or replaces or repositions brackets. The adjustment process is both time consuming and tedious for the patient and more often than not results in patient discomfort for several days following the appointment. Moreover, braces are not aesthetically pleasing and make brushing, flossing, and other dental hygiene procedures difficult.

Aligners comprise clear, removable, polymeric shells having cavities shaped to receive and reposition teeth to produce a final tooth arrangement. Dubbed "invisible braces," aligners offer patients significantly improved aesthetics over braces. Aligners do not require the orthodontists to bend wires or reposition brackets and are generally more comfortable than braces. However, unlike braces, aligners cannot effectively treat all malocclusions. Certain tooth repositioning steps, such as extrusion, translation, and certain rotations, can be difficult or impossible to achieve with aligners. Moreover, because the aligners are removable, success of treatment is highly dependent on patient compliance, which can be unpredictable and inconsistent.

Lingual braces are an alternative to aligners and traditional (buccal) braces and have been gaining popularity in recent years. Two examples of existing lingual braces are the Incognito™ Appliance System (3M United States) and INBRACE® (Swift Health Systems, Irvine, California, USA), each of which consists of brackets and an archwire placed on the lingual, or tongue side, of the teeth. In contrast to traditional braces, lingual braces are virtually invisible, and, unlike aligners, lingual braces are fixed to the patient's teeth and force compliance. These existing lingual technologies, however, also come with several disadvantages. Most notably, conventional lingual appliances still rely on a bracket-archwire system to move the teeth, thus requiring multiple office visits and painful adjustments. For example, lingual technologies have a relatively short inter-bracket distance, which generally makes compliance of the archwire stiffer. As a result, the overall lingual appliance is more sensitive to archwire adjustments and causes more pain for the patient. Moreover, the lingual surfaces of the appliance can irritate the tongue and impact speech, and make the appliance difficult to clean.

Therefore, a need exists for improved orthodontic appliances.

SUMMARY

The subject technology is illustrated, for example, according to various aspects described below, including with reference to FIGS. 1A-18. Various examples of aspects of the subject technology are described as numbered clauses (1, 2, 3, etc.) for convenience. These are provided as examples and do not limit the subject technology.

Clause 1. A method of manufacturing an orthodontic appliance, comprising:
obtaining data corresponding to an original tooth arrangement (OTA) of a patient's teeth,
obtaining data corresponding to a desired final tooth arrangement (FTA) of the patient's teeth;
determining displacements between the OTA data and the FTA data;
based on the determined displacements, determining a configuration of an orthodontic appliance comprising:
an anchor configured to be positioned adjacent the patient's teeth; and
a plurality of arms each extending away from and coupled to the anchor, the arms configured to be secured to the patient's teeth,
wherein, when the appliance is installed, the arms urge individual ones of the patient's teeth from the OTA toward the FTA.

Clause 2. The method of any one of the Clauses herein, wherein determining the configuration of the orthodontic appliance comprises applying a computer-aided algorithm to input data to generate output data corresponding to the configuration of the orthodontic appliance, the input data comprising the displacements between the OTA data and the FTA data.

Clause 3. The method of any one of the Clauses herein, wherein determining the configuration of the orthodontic appliance comprises applying a computer-aided algorithm to input data to generate output data corresponding to the configuration of the orthodontic appliance, the input data comprising a surface of a periodontal ligament or the area of a root of one or more teeth.

Clause 4. The method of any one of the Clauses herein, wherein determining the configuration of the orthodontic appliance comprises applying a computer-aided algorithm to input data to generate output data corresponding to the configuration of the orthodontic appliance, the input data comprising a bone density of the patient.

Clause 5. The method of any one of the Clauses herein, wherein determining the configuration of the orthodontic appliance comprises applying a computer-aided algorithm to input data to generate output data corresponding to the configuration of the orthodontic appliance, the input data comprising one or more biological determinants obtained from saliva, gingival fluid, blood, urine, or mucosa of the patient.

Clause 6. The method of any one of the Clauses herein, wherein determining the configuration of the orthodontic appliance comprises applying a computer-aided algorithm to input data to generate output data corresponding to the configuration of the orthodontic appliance, the input data comprising a gender of the patient.

Clause 7. The method of any one of the Clauses herein, wherein determining the configuration of the orthodontic appliance comprises applying a computer-aided algorithm to input data to generate output data corresponding to the configuration of the orthodontic appliance, the input data comprising an ethnicity of the patient.

Clause 8. The method of any one of the Clauses herein, wherein determining the configuration of the orthodontic appliance comprises applying a computer-aided algorithm to input data to generate output data corresponding to the configuration of the orthodontic appliance, the input data comprising an age of the patient.

Clause 9. The method of any one of the Clauses herein, wherein determining the configuration of the orthodontic appliance comprises applying a computer-aided algorithm to input data to generate output data corresponding to the configuration of the orthodontic appliance, the input data comprising a jaw for which the appliance is to be installed.

Clause 10. The method of any one of the Clauses herein, wherein determining the configuration of the orthodontic appliance comprises applying a computer-aided algorithm to input data to generate output data corresponding to the configuration of the orthodontic appliance, the input data comprising a number of teeth on which the appliance is to be installed.

Clause 11. The method of any one of the Clauses herein, wherein determining the configuration of the orthodontic appliance comprises applying a computer-aided algorithm to input data to generate output data corresponding to the configuration of the orthodontic appliance, the input data comprising mechanical properties of the tissue (lips, tongue, and/or gingiva) and bone adjacent the teeth to be moved.

Clause 12. The method of any one of the Clauses herein, wherein determining the configuration of the orthodontic appliance comprises applying a computer-aided algorithm to input data to generate output data corresponding to the configuration of the orthodontic appliance, the output data comprising a design of one or more of the plurality of arms.

Clause 13. The method of any one of the Clauses herein, wherein determining the configuration of the orthodontic appliance comprises applying a computer-aided algorithm to input data to generate output data corresponding to the configuration of the orthodontic appliance, the output data comprising a width of one or more of the plurality of arms.

Clause 14. The method of any one of the Clauses herein, wherein determining the configuration of the orthodontic appliance comprises applying a computer-aided algorithm to input data to generate output data corresponding to the configuration of the orthodontic appliance, the output data comprising a thickness dimension of the appliance.

Clause 15. The method of any one of the Clauses herein, wherein determining the configuration of the orthodontic appliance comprises applying a computer-aided algorithm to input data to generate output data corresponding to the configuration of the orthodontic appliance, the output data comprising mechanical properties of one or more of the plurality of arms.

Clause 16. The method of any one of the Clauses herein, wherein determining the configuration of the orthodontic appliance comprises applying a computer-aided algorithm to input data to generate output data corresponding to the configuration of the orthodontic appliance, the output data comprising a design of the anchor.

Clause 17. The method of any one of the Clauses herein, wherein determining the configuration of the orthodontic appliance comprises applying a computer-aided algorithm to input data to generate output data corresponding to the configuration of the orthodontic appliance, the output data comprising a width or thickness of the anchor.

Clause 18. The method of any one of the Clauses herein, wherein determining the configuration of the orthodontic appliance comprises applying a computer-aided algorithm to input data to generate output data corresponding to the configuration of the orthodontic appliance, the output data comprising transformational temperature of material in one or more sections of the appliance.

Clause 19. The method of any one of the Clauses herein, wherein determining the configuration of the orthodontic appliance comprises applying a computer-aided algorithm to input data to generate output data corresponding to the configuration of the orthodontic appliance, the output data comprising connection locations between the plurality of arms and the anchor.

Clause 20. The method of any one of the Clauses herein, wherein obtaining the OTA data comprises imaging the patient's teeth.

Clause 21. The method of any one of the Clauses herein, wherein obtaining the OTA data comprises receiving image data of the patient's teeth.

Clause 22. The method of any one of the Clauses herein, wherein obtaining the FTA data comprises receiving the FTA data from one or more remote computing devices.

Clause 23. The method of any one of the Clauses herein, wherein obtaining the FTA data comprises manipulating teeth positions from the OTA to a second arrangement, and generating the FTA data based on the second arrangement.

Clause 24. The method of any one of the Clauses herein, wherein determining the displacements comprises determining displacement along six degrees of freedom.

Clause 25. The method of any one of the Clauses herein, wherein determining the displacements comprises determining longitudinal displacement along at least one of an occlusogingival axis, a buccolingual axis, or a mesiodistal axis.

Clause 26. The method of any one of the Clauses herein, wherein determining the displacements comprises determining rotational displacement along at least one of an occlusogingival axis, a buccolingual axis, or a mesiodistal axis.

Clause 27. The method of any one of the Clauses herein, wherein determining the displacements comprises determining a translation for each tooth of the patient's teeth.

Clause 28. The method of any one of the Clauses herein, wherein determining the displacements comprises determining a rotation for each tooth of the patient's teeth.

Clause 29. The method of any one of the Clauses herein, further comprising determining, for each tooth of the patient's teeth, a force required to achieve the determined displacements.

Clause 30. The method of any one of the Clauses herein, further comprising determining, for each tooth of the patient's teeth, a torque required to achieve the determined displacements.

Clause 31. The method of any one of the Clauses herein, wherein each of the arms is configured to be coupled to a different tooth of the patient's teeth.

Clause 32. The method of any one of the Clauses herein, wherein determining the configuration of the orthodontic appliance comprises selecting, for each tooth of the patient's teeth, an arm configuration configured to apply the force and/or torque required to achieve the determined displacement for the respective tooth.

Clause 33. The method of any one of the Clauses herein, wherein determining the configuration of the orthodontic appliance comprises determining a configuration for one of the plurality of arms configured to achieve the determined displacement for a respective tooth.

Clause 34. The method of any one of the Clauses herein, wherein determining the configuration of the orthodontic appliance comprises selecting an arm design from a library of pre-determined arm designs.

Clause 35. The method of any one of the Clauses herein, wherein determining the configuration of the orthodontic appliance comprises designing a biasing portion of each of the arms to achieve the determined displacement for a respective tooth.

Clause 36. The method of any one of the Clauses herein, further comprising determining a force and a moment to achieve the determined displacement for each tooth, and selecting an arm to achieve the determined force and moment.

Clause 37. The method of any one of the Clauses herein, further comprising obtaining position data corresponding to locations of the patient's teeth in the OTA representing positions at which a plurality of securing members are configured to be attached to the patient's teeth.

Clause 38. A method of manufacturing an orthodontic appliance, comprising:
obtaining three-dimensional (3D) shape data for an appliance;
generating planar shape data based on the 3D shape data;
forming a substantially planar member based on the planar shape data;
manipulating the member into a 3D configuration; and
shape-setting the member in the 3D configuration.

Clause 39. The method of any one of the Clauses herein, wherein the 3D shape data corresponds to a final tooth arrangement (FTA).

Clause 40. The method of any one of the Clauses herein, wherein the 3D shape data corresponds at least in part to a surface of a heat treatment fixture.

Clause 41. The method of any one of the Clauses herein, wherein the 3D shape data defines an anchor and a plurality of arms extending away from the anchor, each of the arms configured to couple to at least one of the patient's teeth.

Clause 42. The method of any one of the Clauses herein, wherein the planar shape data comprises elongate shape data.

Clause 43. The method of any one of the Clauses herein, wherein the planar shape data comprises 2D shape data.

Clause 44. The method of any one of the Clauses herein, wherein generating the planar shape data comprises flattening the 3D shape data.

Clause 45. The method of any one of the Clauses herein, wherein generating the planar shape data comprises converting the 3D shape data into the planar shape data.

Clause 46. The method of any one of the Clauses herein, wherein forming the substantially planar member comprises cutting the substantially planar member from a sheet of material based at least in part on the planar shape data.

Clause 47. The method of any one of the Clauses herein, wherein forming the substantially planar member comprises cutting the substantially planar member from a sheet of metal.

Clause 48. The method of any one of the Clauses herein, wherein forming the substantially planar member comprises cutting the substantially planar member from a sheet of Nitinol.

Clause 49. The method of any one of the Clauses herein, wherein forming the substantially planar member comprises cutting the member from a sheet of material having a thickness of between about 0.1 mm and about 1.0 mm, between about 0.2 mm and about 0.9 mm, between about 0.3 mm and about 0.8 mm, between about 0.4 mm and about 0.7 mm, or about 0.5 mm.

Clause 50. The method of any one of the Clauses herein, wherein forming the substantially planar member comprises cutting the member from a sheet of material having a thickness of less than about 1.5 mm, less than about 1.4 mm, less than about 1.3 mm, less than about 1.2 mm, less than about 1.1 mm, less than about 1.0 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm.

Clause 51. The method of any one of the Clauses herein, wherein forming the substantially planar member comprises cutting the substantially planar member from a sheet of material via at least one of: laser cutting, milling, wire electrical discharge machining, water jetting, punching, or stamping.

Clause 52. The method of any one of the Clauses herein, wherein manipulating the member comprises bending the member.

Clause 53. The method of any one of the Clauses herein, wherein manipulating the member comprises coupling the member to a heat treatment fixture.

Clause 54. The method of any one of the Clauses herein, wherein manipulating the member comprises conforming the member to a surface of a heat treatment fixture.

Clause 55. The method of Clause 53 or REF _Ref34996537 \r \h Clause 54, wherein the heat treatment fixture comprises a surface geometry corresponding to the 3D configuration.

Clause 56. The method of any one of \* MERGEFORMAT Clause 53 to REF _Ref32954387 \r \h Clause 55, further comprising fastening the member to the heat treatment fixture.

Clause 57. The method Clause 56, wherein fastening comprises securing the member to the heat treatment fixture via one or more elongated flexible elements.

Clause 58. The method of any one of the Clauses herein, wherein shape-setting the member comprises heat-setting the member.

Clause 59. The method of any one of the Clauses herein, wherein shape-setting the member comprises heating the member to at least 200 degrees centigrade.

Clause 60. The method of \* MERGEFORMAT Clause 58 or REF Ref32953591 \r \h \* MERGEFORMAT Clause 59, further comprising, after heating the member, cooling the member via liquid quench or air cooling.

Clause 61. The method of any one of Clause 58 to REF _Ref32955511 \r \h Clause 60, further comprising removing the member from the heat treatment fixture.

Clause 62. The method of Clause 61, further comprising, after removing the member from the heat treatment fixture, polishing, electropolishing, electroplating, coating, ultrasonically cleansing, or sterilizing the member.

Clause 63. The method of any one of the Clauses herein, further comprising selectively thinning at least a portion of the planar member.

Clause 64. The method of Clause 63, wherein selectively thinning comprises one or more of: grinding, etching, or machining.

Clause 65. The method of any one of the Clauses herein, further comprising selectively thickening at least a portion of the planar member.

Clause 66. The method of Clause 65, wherein selectively thickening comprises 3D printing, electroplating, or thin-film deposition over at least a portion of the planar member.

Clause 67. A method of manufacturing a heat treatment fixture for an orthodontic appliance, the method comprising:
obtaining final tooth arrangement (FTA) data corresponding to a desired tooth arrangement;
manipulating the FTA data to obtain fixture data defining a geometry of a heat treatment fixture; and
fabricating the heat treatment fixture based at least in part on the fixture data.

Clause 68. The method of any one of the Clauses herein, wherein the FTA data includes securing member positions at which securing members are configured to be placed on each tooth.

Clause 69. The method of Clause 68, wherein the securing members are configured to mate with arms of an orthodontic appliance.

Clause 70. The method of any one of the Clauses herein, wherein the FTA data includes data characterizing a gingiva, and wherein manipulating the modified FTA data comprises changing the dimensions and/or position of the gingiva.

Clause 71. The method of Clause 70, wherein changing the dimensions and/or position of the gingiva comprises expanding the gingiva.

Clause 72. The method of \* MERGEFORMAT Clause 70 or REF Ref32955557 \r \h \* MERGEFORMAT Clause 71, wherein changing the dimensions of the gingiva comprises expanding the gingiva at least in a lingual direction.

Clause 73. The method of any one of \* MERGEFORMAT Clause 70 to REF _Ref32955629 \r \h \* MERGEFORMAT Clause 72, wherein changing the dimensions or position of the gingiva comprises expanding the gingiva by a distance of less than about 1.5 mm, less than about 1.4 mm, less than about 1.3 mm, less than about 1.2 mm, less than about 1.1 mm, less than about 1.0 mm, less than about 0.9 mm, less than about 0.8 mm, less than about 0.7 mm, less than about 0.6 mm, less than about 0.5 mm, less than about 0.4 mess, less than about 0.3 mm, less than about 0.2 mm, or less than about 0.1 mm.

Clause 74. The method of any one of the Clauses herein, wherein manipulating the FTA data includes removing one or more teeth from the FTA data.

Clause 75. The method of any one of the Clauses herein, wherein manipulating the FTA data includes adding a reinforcing element.

Clause 76. The method of any one of the Clauses herein, wherein manipulating the FTA data includes adding a crossbar.

Clause 77. The method of any one of the Clauses herein, wherein manipulating the FTA data changes the geometry of the heat treatment fixture to increase its rigidity.

Clause 78. The method of any one of the Clauses herein, wherein the FTA data includes data characterizing securing members, and wherein manipulating the FTA data comprises modifying the securing member data to change a shape of the securing members.

Clause 79. The method of any one of the Clauses herein, wherein the FTA data includes securing members configured to mate with arms of an orthodontic appliance, and wherein modifying the FTA data comprises changing a shape of the securing members.

Clause 80. The method of Clause 79, wherein changing the shape of the securing members comprises shaping the securing members to mate with arms of the orthodontic appliance and to receive an elongated fastener for coupling the appliance to the heat treatment fixture.

Clause 81. The method of any one of the Clauses herein, wherein fabricating the heat treatment fixture comprises forming the heat treatment fixture of a metal or ceramic material.

Clause 82. The method of any one of the Clauses herein, wherein fabricating the heat treatment fixture comprises forming the heat treatment fixture using one or more of: molding, 3D printing, or casting.

Clause 83. The method of any one of the Clauses herein, further comprising coupling an orthodontic appliance to the heat treatment fixture and subjecting the appliance and the heat treatment fixture to heat.

Clause 84. The Clause 83, wherein subjecting the appliance and the heat treatment fixture to heat comprises heating to at least 200 degrees centigrade.

Clause 85. The method of Clause 84, further comprising, after heating, cooling the appliance and the heat treatment fixture via liquid quench or air cooling.

Clause 86. The method of any one of Clause 83 to REF _Ref32953734 \r \h Clause 85, wherein coupling the orthodontic appliance to the heat treatment fixture comprises wrapping one or more elongated fasteners around the orthodontic appliance and the heat treatment fixture.

Clause 87. A computer-readable medium comprising configured to store instructions that, when executed by one or more processors, cause the one or more processors to perform the method of any one of the Clauses herein.

Clause 88. A device comprising:
one or more processors; and
computer-readable medium comprising configured to store instructions that, when executed by one or more processors, cause the one or more processors to perform the method of any one of the Clauses herein.

Clause 89. An orthodontic appliance manufactured according to a method of any one of the Clauses herein.

Clause 90. A heat treatment fixture manufactured according to a method of any one of the Clauses herein.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
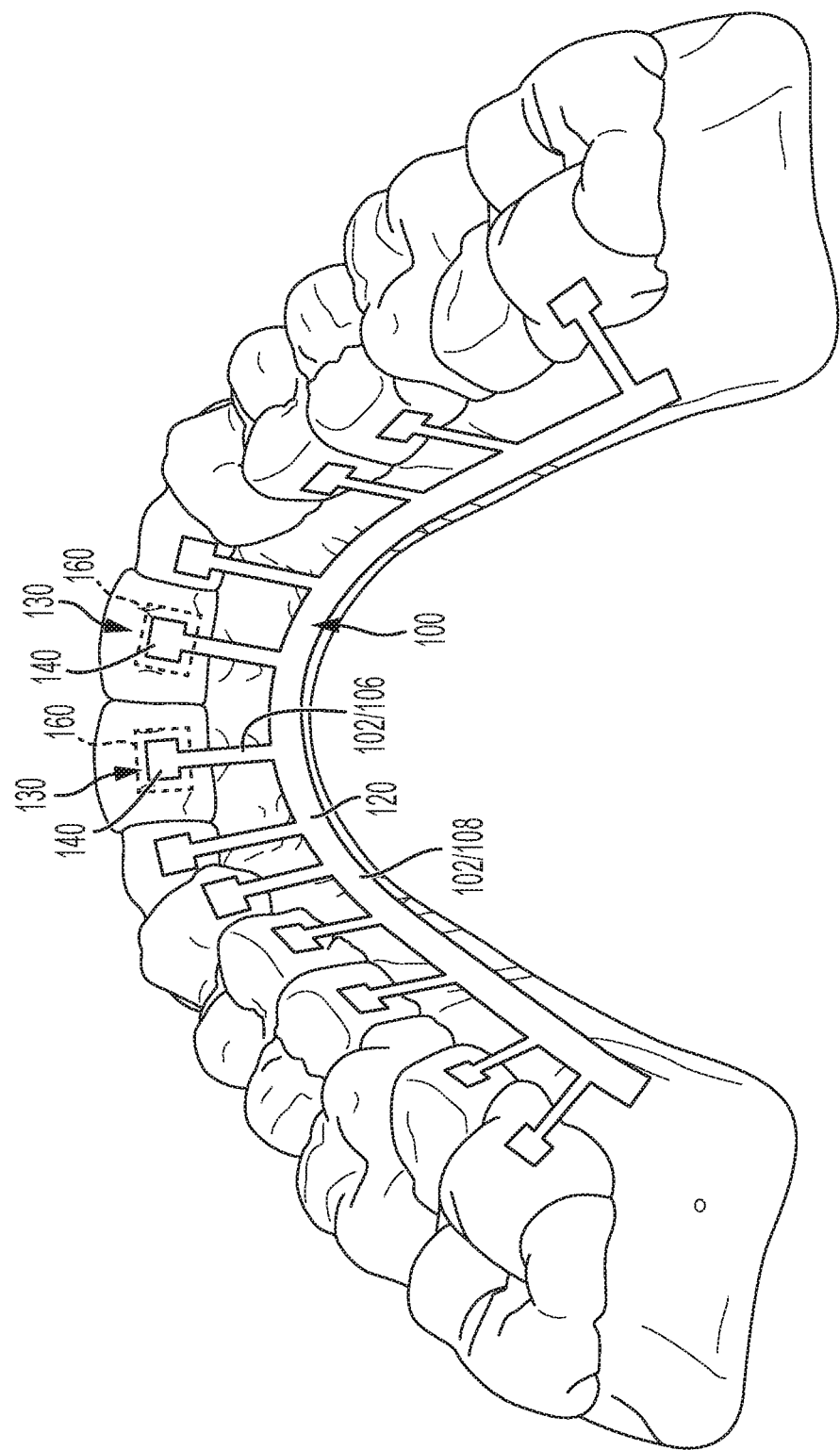
FIG. 1A shows the schematic representation of an orthodontic appliance configured in accordance with the present technology installed in a patient's mouth adjacent the patient's dentition.

The present technology relates generally to orthodontic appliances and associated systems configured to reposition one or more of a patient's teeth. In particular embodiments, the present technology relates to devices, systems, and methods for attaching or securing orthodontic appliances to the teeth, and associated methods for designing and fabricating such appliances. Specific details of several embodiments of the technology are described below with reference to FIGS. 1A-18.

I. Definitions

Terms used herein to provide anatomical direction or orientation are intended to encompass different orientations of the appliance as installed in the patient's mouth, regardless of whether the structure being described is shown installed in a mouth in the drawings. For example, "mesial" means in a direction toward the midline of the patient's face along the patient's curved dental arch; "distal" means in a direction away from the midline of the patient's face along the patient's curved dental arch; "occlusal" means in a direction toward the chewing surfaces of the patient's teeth; "gingival" means in a direction toward the patient's gums or gingiva; "facial" means in a direction toward the patient's lips or cheeks (used interchangeably herein with "buccal" and "labial"); and "lingual" means in a direction toward the patient's tongue.

As used herein, the terms "proximal" and "distal" refer to a position that is closer and farther, respectively, from a given reference point. In many cases, the reference point is a certain connector, such as an anchor, and "proximal" and "distal" refer to a position that is closer and farther, respectively, from the reference connector along a line passing through the centroid of the cross-section of the portion of the appliance branching from the reference connector.

As used herein, the terms "generally," "substantially," "about," and similar terms are used as terms of approximation and not as terms of degree, and are intended to account for the inherent variations in measured or calculated values that would be recognized by those of ordinary skill in the art.

As used herein, the term "operator" refers to a clinician, practitioner, technician or any person or machine that designs and/or manufactures an orthodontic appliance or portion thereof, and/or facilitates the design and/or manufacture of the appliance or portion thereof, and/or any person or machine associated with installing the appliance in the patient's mouth and/or any subsequent treatment of the patient associated with the appliance.

As used herein, the term "force" refers to the magnitude and/or direction of a force, a torque, or a combination thereof.

II. Overview of Orthodontic Appliances of the Present Technology

Figure 1B:
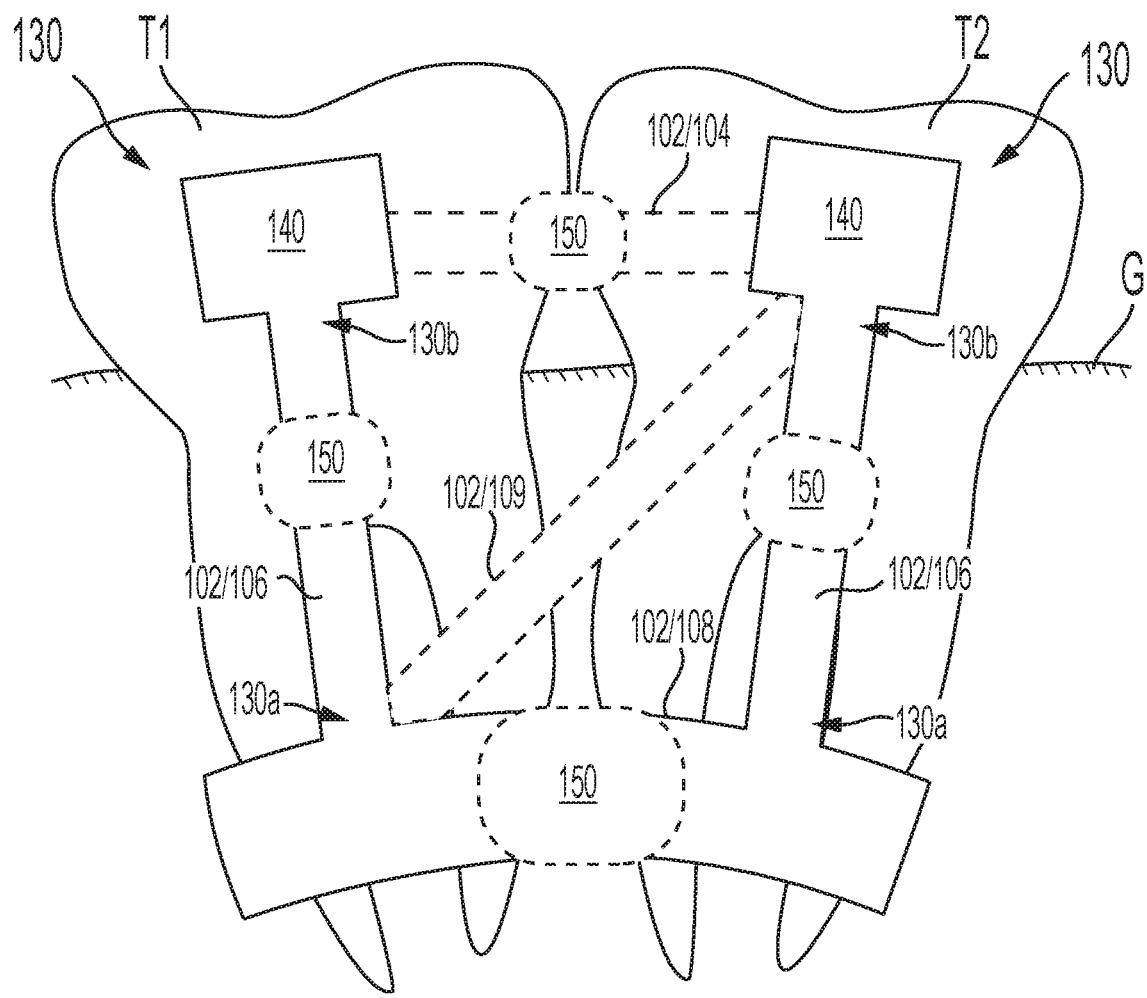
FIG. 1B is a schematic depiction of connection configuration options configured in accordance with embodiments of the present technology.

FIG. 1A is a schematic representation of an orthodontic appliance 100 (or "appliance 100") configured in accordance with embodiments of the present technology, shown positioned in a patient's mouth adjacent the patient's teeth. FIG. 1B is an enlarged view of a portion of the appliance 100. The appliance 100 is configured to be installed within a patient's mouth to impart forces on one or more of the teeth to reposition all or some of the teeth. In some cases, the appliance 100 may additionally or alternatively be configured to maintain a position of one or more teeth. As shown schematically in FIGS. 1A and 1B, the appliance 100 can comprise a deformable member that includes one or more attachment portions 140 (each represented schematically by a box), each configured to be secured to a tooth surface directly or indirectly via a securing member 160. The appliance 100 may further comprise one or more connectors 102 (also depicted schematically), each extending directly between attachment portions 140 ("first connectors 104"), between an attachment portion 140 and one or more other connectors 102 ("second connectors 106"), or between two or more other connectors 102 ("third connectors 108"). Only two attachment portions 140 and two connectors 102 are labeled in FIG. 1A for ease of illustration. As discussed herein, the number, configuration, and location of the connectors 102 and attachment portions 140 may be selected to provide a desired force on one or more of the teeth when the appliance 100 is installed.

The attachment portions 140 may be configured to be detachably coupled to a securing member 160 that is bonded, adhered, or otherwise secured to a surface of one of the teeth to be moved. In some embodiments, one or more of the attachment portions 140 may be directly bonded, adhered, or otherwise secured to a corresponding tooth without a securing member or other connection interface at the tooth. The different attachment portions 140 of a given appliance 100 may have the same or different shape, same or different size, and/or same or different configuration. The attachment portions 140 may comprise any of the attachment portions, bracket connectors, and/or male connector elements disclosed in U.S. Patent Publication No. 2017/0156823 A1, which is incorporated by reference herein in its entirety.

The appliance 100 may include any number of attachment portions 140 suitable for securely attaching the appliance 100 to the patient's tooth or teeth in order to achieve a desired movement. In some examples, multiple attachment portions 140 may be attached to a single tooth. The appliance 100 may include an attachment portion for every tooth, fewer attachment portions than teeth, or more attachment portions 140 than teeth. In these and other embodiments, the appliance 100 one or more of the attachment portions 140 may be configured to be coupled to one, two, three, four, five or more connectors 102.

As previously mentioned, the connectors 102 may comprise one or more first connectors 104 that extend directly between attachment portions 140. The one or more first connectors 104 may extend along a generally mesiodistal dimension when the appliance 100 is installed in the patient's mouth. In these and other embodiments, the appliance 100 may include one or more first connectors 104 that extend along a generally occlusogingival and/or buccolingual dimension when the appliance 100 is installed in the patient's mouth. In some embodiments, the appliance 100 does not include any first connectors 104.

Additionally or alternatively, the connectors 102 may comprise one or more second connectors 106 that extend between one or more attachment portions 140 and one or more connectors 102. The one or more second connectors 106 can extend along a generally occlusogingival dimension when the appliance 100 is installed in the patient's mouth. In these and other embodiments, the appliance 100 may include one or more second connectors 106 that extend along a generally mesiodistal and/or buccolingual dimension when the appliance 100 is installed in the patient's mouth. In some embodiments, the appliance 100 does not include any second connectors 106. In such embodiments, the appliance 100 would only include first connectors 104 extending between attachment portions 140. A second connector 106 and the attachment portion 140 to which it is attached may comprise an "arm," as used herein (such as arm 130 in FIGS. 1A and 1B). In some embodiments, multiple second connectors 106 may extend from the same location along the appliance 100 to the same attachment portion 140. In such cases, the multiple second connectors 106 and the attachment portion 140 together comprise an "arm," as used herein. The use of two or more connectors to connect two points on the appliance 100 enables application of a greater force (relative to a single connector connecting the same points) without increasing the strain on the individual connectors. Such a configuration is especially beneficial given the spatial constraints of the fixed displacement treatments herein.

Additionally or alternatively, the connectors 102 may comprise one or more third connectors 108 that extend between two or more other connectors 102. The one or more third connectors 108 may extend along a generally mesiodistal dimension when the appliance 100 is installed in the patient's mouth. In these and other embodiments, the appliance 100 may include one or more third connectors 108 that extend along a generally occlusogingival and/or buccolingual dimension when the appliance 100 is installed in the patient's mouth. In some embodiments, the appliance 100 does not include any third connectors 108. One, some, or all of the third connectors 108 may be positioned gingival to one, some, or all of the first connectors 104. In some embodiments, the appliance 100 includes a single third connector 108 that extends along at least two adjacent teeth and provides a common attachment for two or more second connectors 106. In several embodiments, the appliance 100 includes multiple non-contiguous third connectors 108, each extending along at least two adjacent teeth.

As shown in FIG. 1A, in some embodiments the appliance 100 may be configured such that all or a portion of one, some, or all of the connectors 102 disposed proximate the patient's gingiva when the appliance 100 is installed within the patient's mouth. For example, one or more third connectors 108 may be configured such that all or a portion of the one or more third connectors 108 is positioned below the patient's gum line and adjacent to but spaced apart from the gingiva. In many cases it may be beneficial to provide a small gap (e.g., 0.5 mm or less) between the third connector(s) 108 and the patient's gingiva, as contact between the third connector(s) 108 (or any portion of the appliance 100) and the gingiva can cause irritation and patient discomfort. In some embodiments, all or a portion of the third connector(s) 108 is configured to be in direct contact with the gingiva when the appliance 100 is disposed in the patient's mouth. Additionally or alternatively, all or a portion of one or more first connectors 104 and/or second connectors 106 may be configured to be disposed proximate the gingiva.

According to some embodiments, one or more connectors 102 may extend between an attachment portion 140 or connector 102 and a joint comprising (a) two or more connectors 102, (b) two or more attachment portions 140, or (c) at least one attachment portion 140 and at least one connector 102. According to some embodiments, one or more connectors 102 may extend between a first joint comprising (a) two or more connectors 102, (b) two or more attachment portions 140, or (c) at least one attachment member and at least one connector 102, and a second joint comprising (a) two or more connectors 102, (b) two or more attachment portions 140, or (c) at least one attachment portion 140 and at least one connector 102. An example of a connector 102 extending between (a) a joint between a second and third connector 106, 108, and (b) a joint between a second connector 106 and an attachment portion 140 is depicted schematically and labeled 109 in FIG. 1B.

Each of the connectors 102 may be designed to have a desired stiffness so that an individual connector 102 or combination of connectors 102 imparts a desired force on one or more of the teeth. In many cases, the force applied by a given connector 102 may be governed by Hooke's Law, or F=kxx, where F is the restoring force exerted by the connector 102, k is the stiffness coefficient of the connector 102, and x is the displacement. In the most basic example, if a connector 102 does not exist between two points on the appliance 100, then the stiffness coefficient along that path is zero and no forces are applied. In the present case, the individual connectors 102 of the present technology may have varying non-zero stiffness coefficients. For example, one or more of the connectors 102 may be rigid (i.e., the stiffness coefficient is infinite) such that the connector 102 will not flex or bend between its two end points. In some embodiments, one or more of the connectors 102 may be "flexible" (i.e., the stiffness coefficient is non-zero and positive) such that the connector 102 can deform to impart (or absorb) a force on the associated tooth or teeth or other connector 102.

In some embodiments it may be beneficial to include one or more rigid connectors between two or more teeth. A rigid connector 102 is sometimes referred to herein as a "rigid bar" or an "anchor." Each rigid connector 102 may have sufficient rigidity to hold and maintain its shape and resist bending. The rigidity of the connector 102 can be achieved by selecting a particular shape, width, length, thickness, and/or material. Connectors 102 configured to be relatively rigid may be employed, for example, when the tooth to be connected to the connector 102 or arm is not to be moved (or moved by a limited amount) and can be used for anchorage. Molar teeth, for example, can provide good anchorage as molar teeth have larger roots than most teeth and thus require greater forces to be moved. Moreover, anchoring one or more portions of the appliance 100 to multiple teeth is more secure than anchoring to a single tooth. As another example, a rigid connection may be desired when moving a group of teeth relative to one or more other teeth. Consider, for instance, a case in which the patient has five teeth separated from a single tooth by a gap, and the treatment plan is to close the gap. The best course of treatment is typically to move the one tooth towards the five teeth, and not vice versa. In this case, it may be beneficial to provide one or more rigid connectors between the five teeth. For all of the foregoing reasons and many others, the appliance 100 may include one or more rigid first connectors 104, one or more rigid second connectors 106, and/or one or more rigid third connectors 108.

In these and other embodiments, the appliance 100 may include one or more flexible first connectors 104, one or more flexible second connectors 106, and/or one or more flexible third connectors 108. Each flexible connector 102 may have a particular shape, width, thickness, length, material, and/or other parameters to provide a desired degree of flexibility. According to some embodiments of the present technology, the stiffness of a given connector 102 may be tuned via incorporation of a one or more resiliently flexible biasing portions 150. As shown schematically in FIG. 1B, one, some, or all of the connectors 102 may include one or more biasing portion 150, such as springs, each configured to apply a customized force specific to the tooth to which it is attached.

Figure 1C:
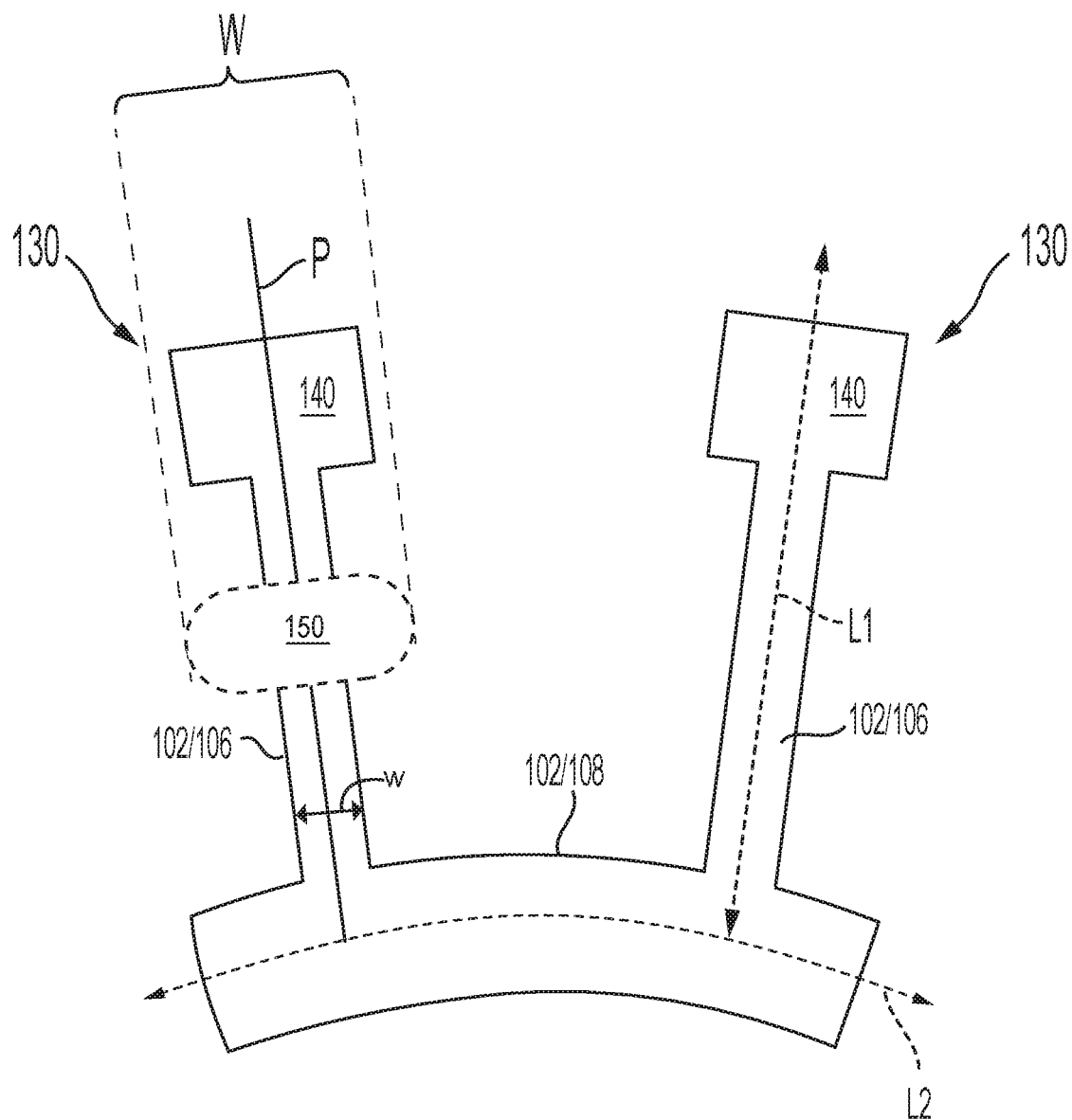
FIG. 1C is a schematic depiction of a portion of an appliance configured in accordance with embodiments of the present technology.

As depicted in the schematic shown in FIG. 1C, the biasing portion(s) 150 may extend along all or a portion of the longitudinal axis L1 of the respective connector 102 (only the longitudinal axis L1 for second connector 106 and the longitudinal axis L2 for third connector 108 is labeled in FIG. 1C). The direction and magnitude of the force and torque applied on a tooth by a biasing portion 150 depends, at least in part, on the shape, width, thickness, length, material, shape set conditions, and other parameters of the biasing portion 150. As such, one or more aspects of the biasing portion 150 (including the aforementioned parameters) may be varied so that the corresponding arm 130, connector 102, and/or biasing portion 150 produces a desired tooth movement when the appliance 100 is installed in the patient's mouth. Each arm 130 and/or biasing portion 150 may be designed to move one or more teeth in one, two, or all three translational directions (i.e., mesiodistal, buccolingual, and occlusogingival) and/or in one, two, or all three rotational directions (i.e., buccolingual root torque, mesiodistal angulation and mesial out-in rotation).

The biasing portions 150 of the present technology can have any length, width, shape, and/or size sufficient to move the respective tooth towards a desired position. In some embodiments, one, some, or all of the connectors 102 may have one or more inflection points along a respective biasing portion 150. The connectors 102 and/or biasing portions 150 may have a serpentine configuration such that the connector 102 and/or biasing portion 150 doubles back on itself at least one or more times before extending towards the attachment portion 140. For example, in some embodiments the second connectors 106 double back on themselves two times along the biasing portion 150, thereby forming first and second concave regions facing in generally different directions relative to one another. The open loops or overlapping portions of the connector 102 corresponding to the biasing portion 150 may be disposed on either side of a plane P (FIG. 1C) bisecting an overall width W (FIG. 1C) of the arm 130 and/or connector 102 such that the extra length of the arm 130 and/or connector 102 is accommodated by the space medial and/or distal to the arm 130 and/or connector 102. This allows the arm 130 and/or connector 102 to have a longer length (as compared to a linear arm) to accommodate greater tooth movement, despite the limited space in the occlusal-gingival or vertical dimension between any associated third connector 108 and the location at which the arm 130 attaches to the tooth.

It will be appreciated that the biasing portion 150 may have other shapes or configurations. For example, in some embodiments the connector 102 and/or biasing portion 150 may include one or more linear regions that zig-zag towards the attachment portion 140. One, some, or all of the connectors 102 and/or biasing portions 150 may have only linear segments or regions, or may have a combination of curved and linear regions. In some embodiments, one, some, or all of the connectors 102 and/or biasing portions 150 do not include any curved portions.

According to some examples, a single connector 102 may have multiple biasing portions 150 in series along the longitudinal axis of the respective connector 102. In some embodiments, multiple connectors 102 may extend between two points along the same or different paths. In such embodiments, the different connectors 102 may have the same stiffness or different stiffnesses.

In those embodiments where the appliance 100 has two or more connectors 102 with biasing portions 150, some, none, or all of the connectors 102 may have the same or different lengths, the same or different widths, the same or different thicknesses, the same or different shapes, and/or may be made of the same or different materials, amongst other properties. In some embodiments, less than all of the connectors 102 have biasing portions 150. Connectors 102 without biasing portions 150 may, for example, comprise one or more rigid connections between a rigid third connector 108 and the attachment portion 140. In some embodiments, none of the connectors 102 of the appliance 100 have a biasing portion 150.

According to some embodiments, for example as depicted schematically in FIG. 1A, the appliance 100 may include a single, continuous, substantially rigid third connector (referred to as "anchor 120") and a plurality of flexible arms 130 extending away from the anchor 120. When the appliance 100 is installed in the patient's mouth, each of the arms 130 may connect to a different one of the teeth to be moved and exerts a specific force on its respective tooth, thereby allowing an operator to move each tooth independently. Such a configuration provides a notable improvement over traditional braces in which all of the teeth are connected by a single archwire, such that movement of one tooth can cause unintentional movement of one or more nearby teeth. As discussed in greater detail herein, the independent and customized tooth movement enabled by the appliances of the present technology allows the operator to move the teeth from an original tooth arrangement ("OTA") to a final tooth arrangement ("FTA") more efficiently, thereby obviating periodic adjustments, reducing the number of office visits, and reducing or eliminating patient discomfort, and reducing the overall treatment time (i.e., the length of time the appliance is installed in the patient's mouth) by at least 50% relative to the overall treatment time for traditional braces.

The anchor 120 may comprise any structure of any shape and size configured to comfortably fit within the patient's mouth and provide a common support for one or more of the arms 130. In many embodiments, the anchor 120 is disposed proximate the patient's gingiva when the appliance 100 is installed within the patient's mouth, for example as shown in FIG. 1B. For instance, the appliance may be designed such that, when installed in the patient's mouth, all or a portion of the anchor 120 is positioned below the patient's gum line and adjacent but spaced apart from the gingiva. In many cases it may be beneficial to provide a small gap (e.g., 0.5 mm or less) between the anchor 120 (or any portion of the appliance 100) and the patient's gingiva as contact between the anchor 120 and the gingiva can cause irritation and patient discomfort. In some embodiments, all or a portion of the anchor 120 is configured to be in contact with the gingiva when the appliance 100 is disposed in the patient's mouth.

The anchor 120 may be significantly more rigid than the arms 130 such that the equal and opposite forces experienced by each of the arms 130 when exerting a force on its respective tooth are countered by the rigidity of the anchor 120 and the forces applied by the other arms 130, and do not meaningfully affect the forces on other teeth. As such, the anchor 120 effectively isolates the forces experienced by each arm 130 from the rest of the arms 130, thereby enabling independent tooth movement.

According to some embodiments, for example as shown schematically in FIGS. 1A and 1B, the anchor 120 comprises an elongated member having a longitudinal axis L2 (see FIG. 1C) and forming an arched shape configured to extend along a patient's jaw when the appliance 100 is installed. In these and other embodiments, the anchor 120 may be shaped and sized to span two or more of the patient's teeth when positioned in the patient's mouth. In some examples, the anchor 120 includes a rigid, linear bar, or may comprise a structure having both linear and curved segments. In these and other embodiments, the anchor 120 may extend laterally across all or a portion of the patient's mouth (e.g., across all or a portion of the palate, across all or a portion of the lower jaw, etc.) and/or in a generally anterior-posterior direction. Moreover, the appliance 100 may comprise a single anchor or multiple anchors. For example, the appliance 100 may comprise multiple, discrete, spaced apart anchors, each having two or more arms 130 extending therefrom. In these and other embodiments, the appliance 100 may include one or more other connectors extending between adjacent arms 130.

Any and all of the features discussed above with respect to anchor 120 may apply to any of the third connectors 108 disclosed herein.

As shown in FIG. 1B, each of the arms 130 may extend between a proximal or first end portion 130a and a distal or second end portion 130b, and may have a longitudinal axis L extending between the first end portion 130a and the second end portion 130b. The first end portion 130a of one, some, or all of the arms 130 may be disposed at the anchor 120. In some embodiments, one, some, or all of the arms 130 are integral with the anchor 120 such that the first end portion 130a of such arms are continuous with the anchor 120. The arms 130 may extend from the anchor 120 at spaced intervals along the longitudinal axis L2 of the anchor 120, as shown in FIG. 1A. In some embodiments, the arms 130 may be spaced at even intervals relative to each other, or at uneven intervals relative to each other, along the longitudinal axis L2 of the anchor 120.

One, some, or all of the arms 130 may include an attachment portion 140 at or near the second end portion 130b. In some embodiments, for example as shown in FIGS. 1A-1C, one or more of the arms 130 is cantilevered from the anchor 120 such that the second end portion 130b of the cantilevered arm(s) 130 has a free distal end portion 130b. In these and other embodiments, a distal terminus of the attachment portion 140 may coincide with a distal terminus of the arm 130. The attachment portion 140 may be configured to detachably couple the respective arm 130 to a securing member (e.g., a bracket) that is bonded, adhered, or otherwise secured to a surface of one of the teeth to be moved. In some embodiments, the attachment portion 140 may be directly bonded, adhered, or otherwise secured to a corresponding tooth without a securing member or other connection interface at the tooth.

Referring to still to FIGS. 1A and 1B, one, some, or all of the arms 130 may include one or more resiliently flexible biasing portions 150, such as springs, each configured to apply a customized force, torque or combination of force and torque specific to the tooth to which it is attached. The biasing portion(s) 150 may extend along all or a portion of the longitudinal axis L1 of the respective arm 130 between the anchor 120 and the attachment portion 140. The direction and magnitude of the force and torque applied on a tooth by a biasing portion 150 depends, at least in part, on the shape, width, thickness, length, material, shape set conditions, and other parameters of the biasing portion 150. As such, one or more aspects of the arm 130 and/or biasing portion 150 (including the aforementioned parameters) may be varied so that the arm 130 and/or biasing portion 150 produce a desired tooth movement when the appliance 100 is installed in the patient's mouth. Each arm 130 and/or biasing portion 150 may be designed to move one or more teeth in one, two, or all three translational directions (i.e., mesiodistal, buccolingual, and occlusogingival) and/or in one, two, or all three rotational directions (i.e., buccolingual root torque, mesiodistal angulation and mesial out-in rotation).

The biasing portions 150 of the present technology can have any length, width, shape, and/or size sufficient to move the respective tooth towards a desired FTA. In some embodiments, one, some, or all of the arms 130 may have one or more inflection points along a respective biasing portion 150. The arms 130 and/or biasing portions 150 may have a serpentine configuration such that the arm 130 and/or biasing portion 150 doubles back on itself at least one or more times before extending towards the attachment portion 140. In FIG. 1B, the arm 130 doubles back on itself two times along the biasing portion 150, thereby forming first and second concave regions facing in generally different directions relative to one another. The open loops or overlapping portions of the arm 130 corresponding to the biasing portion 150 may be disposed on either side of a plane P bisecting an overall width W of the arm 130 such that the extra length of the arm 130 is accommodated by the space medial and/or distal to the arm 130. This allows the arm 130 to have a longer length (as compared to a linear arm) to accommodate greater tooth movement, despite the limited space in the occlusal-gingival or vertical dimension between the anchor 120 and the location at which the arm 130 attaches to the tooth.

It will be appreciated that the biasing portion 150 may have other shapes or configurations. For example, in some embodiments the arm 130 and/or biasing portion 150 may include one or more linear regions that zig-zag towards the attachment portion 140. One, some, or all of the arms 130 and/or biasing portions 150 may have only linear segments or regions, or may have a combination of curved and linear regions. In some embodiments, one, some, or all of the arms 130 and/or biasing portions 150 do not include any curved portions.

According to some examples, a single arm 130 may have multiple biasing portions 150. The multiple biasing portions 150 may be in series along the longitudinal axis L1 of the respective arm 120. In some embodiments, multiple arms 130 may extend in parallel between two points along the same path or along different paths. In such embodiments, the different arms 130 may have the same stiffness or different stiffnesses.

In those embodiments where the appliance 100 has two or more arms 130 with biasing portions 150, some, none, or all of the arms 130 may have the same or different lengths, the same or different widths, the same or different thicknesses, the same or different shapes, and/or may be made of the same or different materials, amongst other properties. In some embodiments, less than all of the arms 130 have biasing portions 150. Arms 130 without biasing portions 150 may, for example, comprise one or more rigid connections between the anchor 120 and the attachment portion 140. In some embodiments, none of the arms 130 of the appliance 100 have a biasing portion 150.

The appliances of the present technology may include any number of arms 130 suitable for repositioning the patient's teeth while taking into account the patient's comfort. Unless explicitly limited to a certain number of arms in the specification, the appliances of the present technology may comprise a single arm, two arms, three arms, five arms, ten arms, sixteen arms, etc. In some examples, one, some, or all of the arms 130 of the appliance may be configured to individually connect to more than one tooth (i.e., a single arm 130 may be configured to couple to two teeth at the same time). In these and other embodiments, the appliance 100 may include two or more arms 130 configured to connect to the same tooth at the same time.

Any portion of the appliances of the present technology may include a biasing portion 150. For example, in some embodiments, portions thereof (e.g., the anchor(s), the arm(s), the biasing portion(s), the attachment portion(s), the link(s), etc.) may comprise one or more superelastic materials.

Additional details related to the individual directional force(s) applied via the biasing portion 150 or, more generally the arm 130, are described in U.S. Patent Publication No. 2017/0156823 A1, the disclosure of which is incorporated by reference herein in its entirety.

The appliances disclosed herein and/or any portion thereof (e.g., the anchor(s), the arm(s), the biasing portion(s), the attachment portion(s), the link(s), etc.) may comprise one or more superelastic materials. The appliances disclosed herein and/or any portion thereof (e.g., the anchor(s), the arm(s), the biasing portion(s), the attachment portion(s), the link(s), etc.) may comprise Nitinol, stainless steel, beta-titanium, cobalt chrome, MP35N, 35N LT, one or more metal alloys, one or more polymers, one or more ceramics, and/or combinations thereof.

Figure 2B:
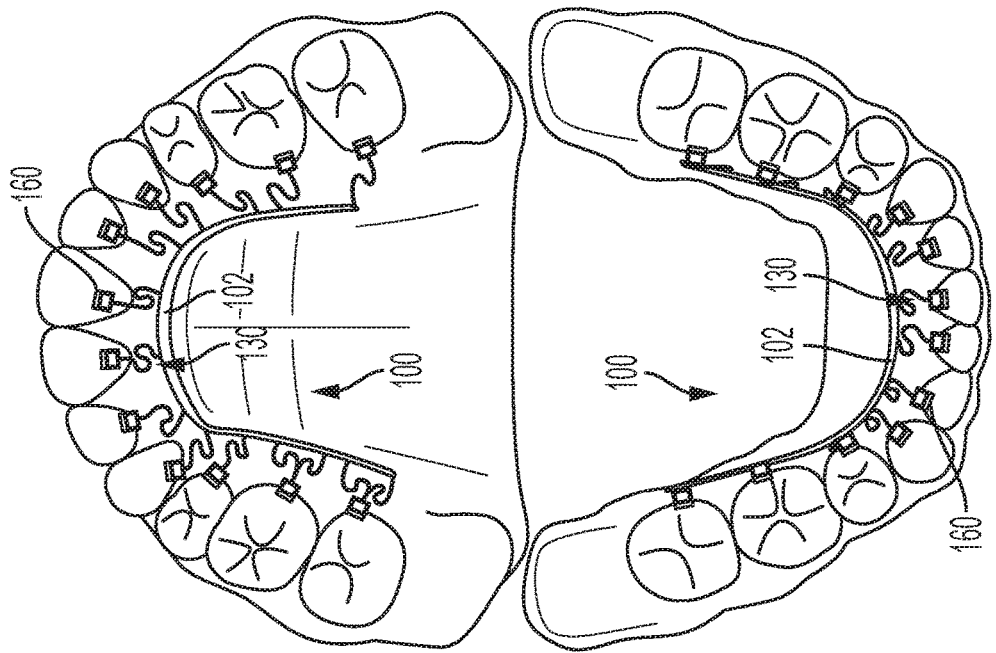
FIGS. 2A and 2B are elevation views of an appliance configured in accordance with several embodiments of the present technology installed in an upper and lower jaw of a patient's mouth with the patient's teeth in an original tooth arrangement and a final tooth arrangement, respectively.
Figure 2A:
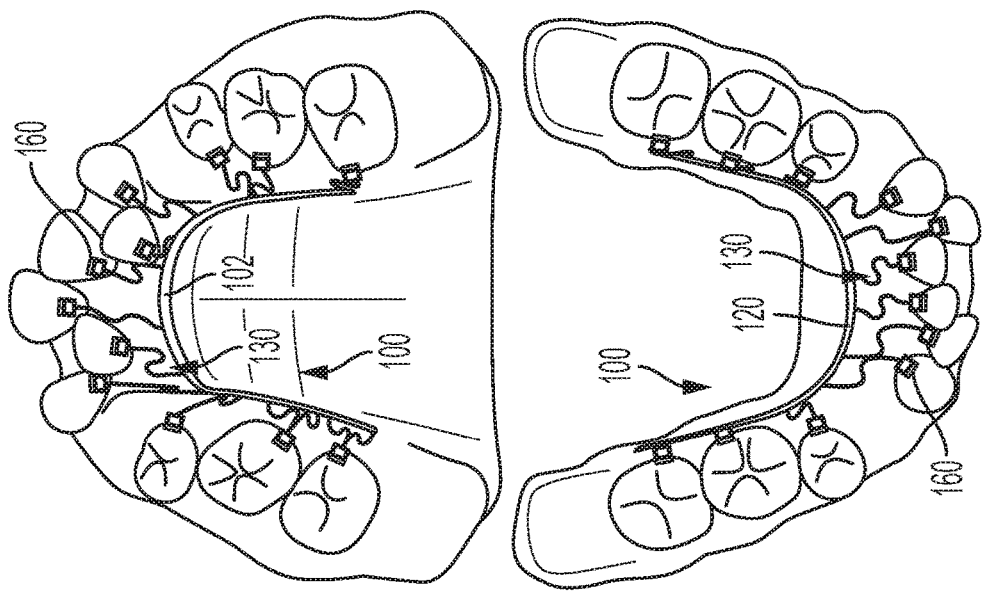
Figure 2C:
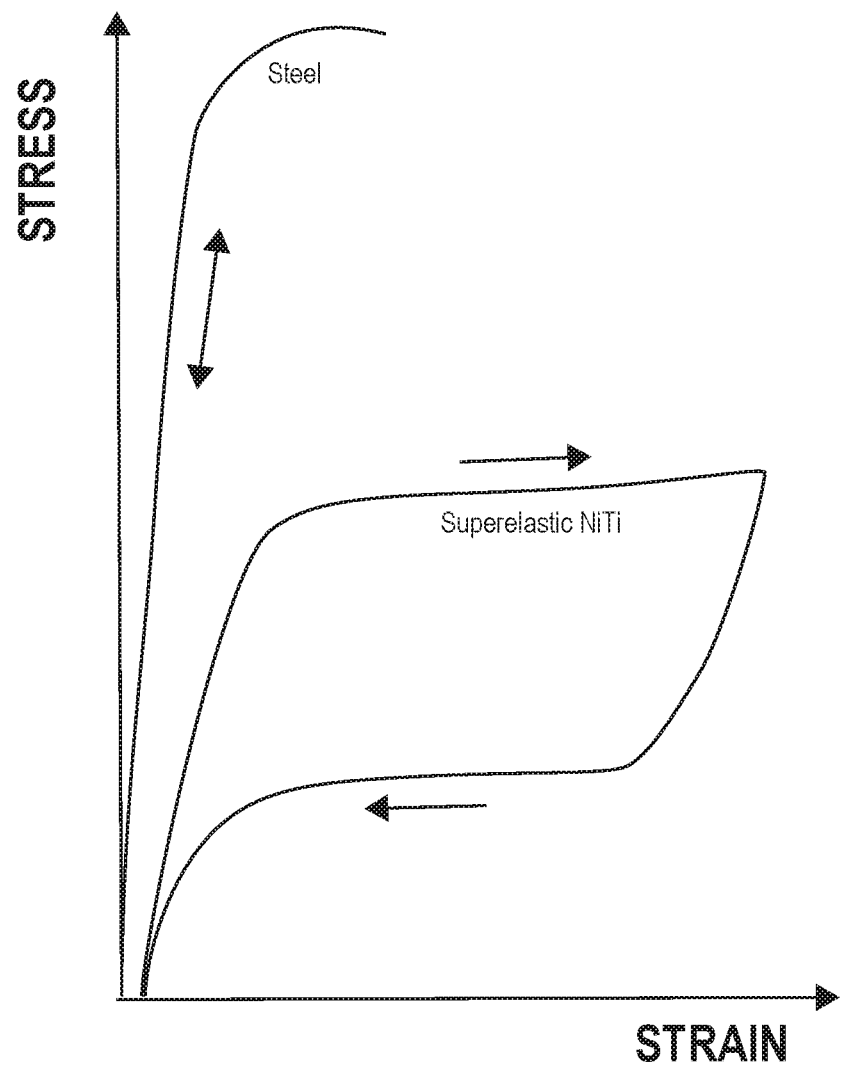
FIG. 2C is a graph showing the stress-strain curves for nitinol and steel.

FIGS. 2A and 2B are elevation views of the appliance 100 installed on both the upper and lower arches of a patient's mouth M with the arms 130 coupled to securing members 160 attached to the lingual surfaces of the teeth. It will be appreciated that the appliance 100 of one or both of the upper and lower arches may be positioned proximate a buccal side of a patient's teeth, and that the securing elements 160 and/or arms 130 may alternatively be coupled to the buccal surface of the teeth.

FIG. 2A shows the teeth in an OTA with the arms 130 in a deformed or loaded state, and FIG. 2B shows the teeth in the FTA with the arms 130 in a substantially unloaded state. When the arms 130 are initially secured to the securing members 160 when the teeth are in the OTA, the arms 130 are forced to take a shape or path different than their "as designed" configurations. Because of the inherent memory of the resilient biasing portions 150, the arms 130 impart a continuous, corrective force on the teeth to move the teeth towards the FTA, which is where the biasing portions 150 are in their as-designed or unloaded configurations. As such, tooth repositioning using the appliances of the present technology can be accomplished in a single step, using a single appliance. In addition to enabling fewer office visits and a shorter treatment time, the appliances of the present technology greatly reduce or eliminate the pain experienced by the patient as the result of the teeth moving as compared to braces. With traditional braces, every time the orthodontist makes an adjustment (such as installing a new archwire, bending the existing archwire, repositioning a bracket, etc.), the affected teeth experience a high force which is very painful for the patient. Over time, the applied force weakens until eventually a new wire is required. The appliances of the present technology, however, apply a movement-generating force on the teeth continuously while the appliance is installed, which allows the teeth to move at a slower rate that is much less painful (if painful at all) for the patient. Even though the appliances disclosed herein apply a lower and less painful force to the teeth, because the forces being applied are continuous and the teeth can move independently (and thus more efficiently), the appliances of the present technology arrive at the FTA faster than traditional braces or aligners, as both alternatives require intermediate adjustments.

In many embodiments, the movement-generating force is lower than that applied by traditional braces. In those embodiments in which the appliance comprises a superelastic material (such as nitinol), the superelastic material behaves like a constant force spring for certain ranges of strain, and thus the force applied does not drop appreciably as the tooth moves. For example, as shown in the stress-strain curves of nitinol and steel in FIG. 2C, the curve for nitinol is relatively flat compared to that of steel. Thus, the superelastic connectors, biasing portions, and/or arms of the present technology apply essentially the same stress for many different levels of strain (e.g., deflection). As a result, the force applied to a given tooth stays constant as the teeth move during treatment, at least up until the teeth are very close or in the final arrangement. The appliances of the present technology are configured to apply a force just below the pain threshold, such that the appliance applies the maximum non-painful force to the tooth (or teeth) at all times during tooth movement. This results in the most efficient (i.e., fastest) tooth movement without pain.

In some embodiments, tooth repositioning may involve multiple steps performed progressively, by using multiple appliances. Embodiments involving multiple steps (or multiple appliances, or both) may include one or more intermediate tooth arrangements (ITAs) between an original tooth arrangement (OTA) and a desired final tooth arrangement (FTA) Likewise, the appliances disclosed herein may be designed to be installed after a first or subsequently used appliance had moved the teeth from an OTA to an ITA (or from one ITA to another ITA) and was subsequently removed. Thus, the appliances of the present technology may be designed to move the teeth from an ITA to an FTA (or to another ITA). Additionally or alternatively, the appliances may be designed to move the teeth from an OTA to an ITA, or from an OTA to an FTA without changing appliances at an ITA.

In some embodiments, the appliances disclosed herein may be configured such that, once installed on the patient's teeth, the appliance cannot be removed by the patient. In some embodiments, the appliance may be removable by the patient.

Any of the example appliances or appliance portions described herein may be made of any suitable material or materials, such as, but not limited to nitinol, stainless steel, beta-titanium, cobalt chrome or other metal alloy, polymers or ceramics, and may be made as a single, unitarily-formed structure or, alternatively, in multiple separately formed components connected together in single structure. However, in particular examples, the rigid bars, bracket connectors and loop or curved features of an appliance (or portion of an appliance) described in those examples are made by cutting a two dimensional (2D) form of the appliance from a 2D sheet of material and bending the 2D form into a desired 3D shape of the appliance, according to processes as described in more detail below. Additionally or alternatively, such appliances (or portions of appliances) can be formed using any suitable techniques, including those described in U.S. Patent Publication No. 2017/0156823 A1, which is hereby incorporated by reference in its entirety.

III. Selected Methods for Manufacturing Orthodontic Appliances and Fixtures

Figure 3:
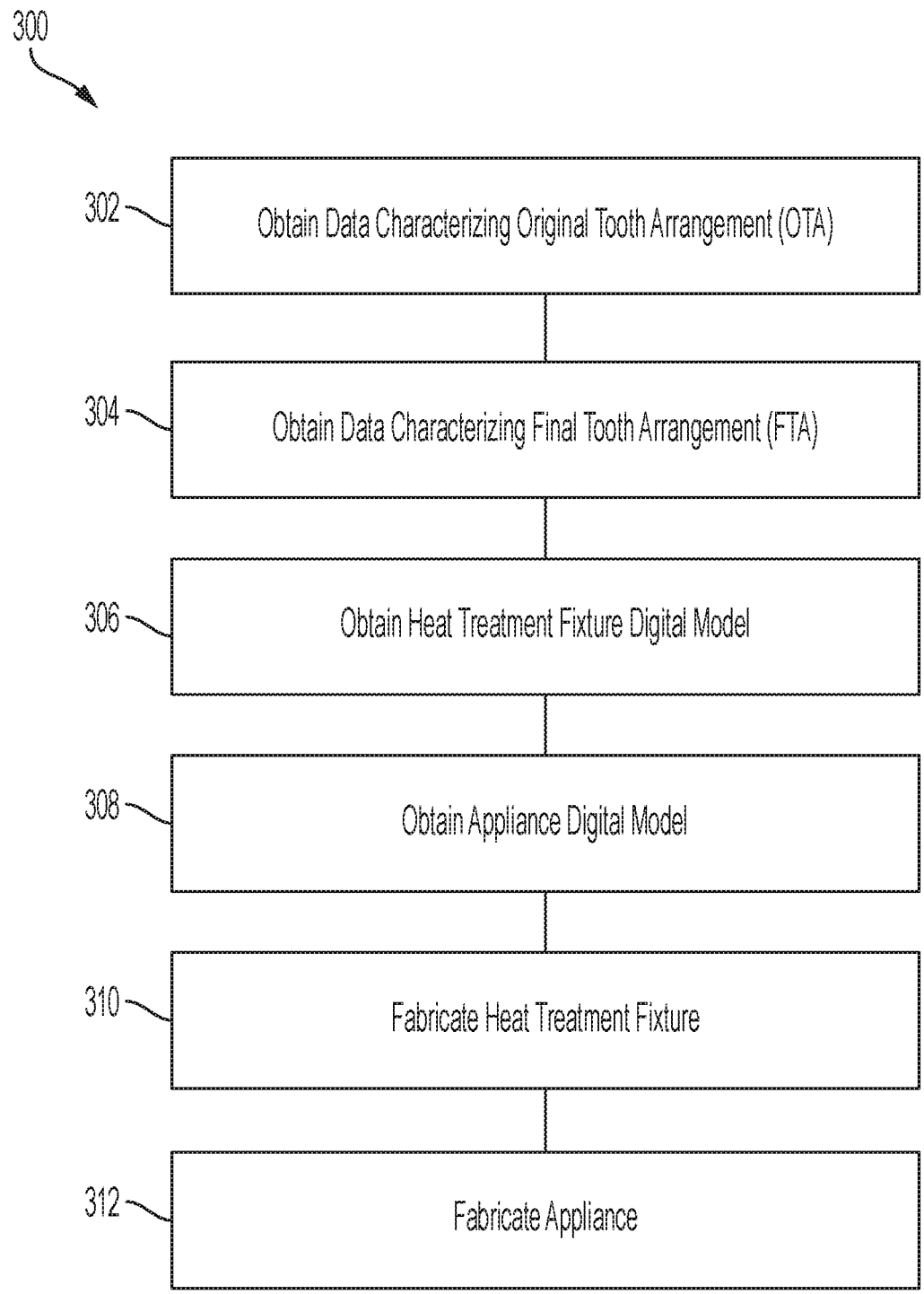
FIG. 3 depicts an example method of manufacturing an orthodontic appliance in accordance with the present technology.

FIG. 3 illustrates an example process 300 for designing and fabricating an orthodontic appliance as described elsewhere herein. The particular processes described herein are exemplary only, and may be modified as appropriate to achieve the desired outcome (e.g., the desired force applied to each tooth by the appliance, the desired material properties of the appliance, etc.). In various embodiments, other suitable methods or techniques can be utilized to fabricate an orthodontic appliance. Moreover, although various aspects of the methods disclosed herein refer to sequences of steps, in various embodiments the steps can be performed in different orders, two or more steps can be combined together, certain steps may be omitted, and additional steps not expressly discussed can be included in the process as desired.

As noted above, in some embodiments an orthodontic appliance is configured to be coupled to a patient's teeth while the teeth are in an original tooth arrangement (OTA). In this position, elements of the appliance exert customized loads on individual teeth to urge them toward a desired final tooth arrangement (FTA). For example, an arm 130 of the appliance 100 can be coupled to a tooth and configured to apply a force so as to urge the tooth in a desired direction toward the FTA. In one example, an arm 130 of the appliance 100 can be configured to apply a tensile force that urges the tooth lingually along the facial-lingual axis. By selecting the appropriate dimensions, shape, shape set, material properties, and other aspects of the arms 130, a customized load can be applied to each tooth to move each tooth from its OTA toward its FTA. In some embodiments, the arms 130 are each configured such that little or no force is applied once the tooth to which the arm 130 is coupled has achieves its FTA. In other words, the appliance 100 can be configured such that the arms 130 are at rest in the FTA state.

As shown in FIG. 3, the process 300 can begin at block 302 with obtaining data (e.g., position data) characterizing the patient's original tooth arrangement (OTA). In some embodiments, the operator may obtain a digital representation of the patient's OTA, for example using optical scanning, cone beam computed tomography (CBCT), scanning of patient impressions, or other suitable imaging technique to obtain position data of the patient's teeth, gingiva, and optionally other adjacent anatomical structures while the patient's teeth are in the original or pre-treatment condition.

The process 300 continues at block 304 with obtaining data (e.g., position data) characterizing the patient's intended or desired final tooth arrangement (FTA). The data characterizing the FTA can include coordinates (e.g., X,Y,Z coordinates) for each of the patient's teeth and the gingiva, Additionally or alternatively, such data can include positioning of each of the patient's teeth relative to other ones of the patient's teeth and/or the gingiva. In some embodiments, the operator can obtain a digital representation of the patient's FTA, for example, an FTA digital model generated using segmentation software (e.g., iROK Digital Dentistry Studio) to create individual virtual teeth and gingiva from the OTA data. In some embodiments, digital models of the securing members 160 can be added to the segmented OTA digital model (e.g., by an operator selecting positions on the lingual surface (or other suitable surface) for placement of securing members 160 thereon). Suitable software can be used to move the virtual teeth with the attached securing members 160 from the OTA to a desired final position (e.g., the FTA), with or without the securing members digital models included.

At block 306, a heat treatment fixture digital model can be obtained. In some embodiments, the heat treatment fixture digital model can correspond to and/or be derived from the FTA digital model. For example, the FTA digital model can be modified (e.g., using MeshMixer or other suitable modeling software) in a variety of ways to render a model suitable for manufacturing a heat treatment fixture. In some embodiments, the FTA digital model can be modified to replace the securing members 160 (which are configured to couple to arms 130 of an appliance 100 (FIGS. 2A and 2B)) with hook-like members (which can be configured to facilitate temporary coupling of the heat treatment fixture to the appliance for shape-setting). Additionally or alternatively, the FTA digital model can be modified to enlarge or thicken the gingiva, to remove one or more of the teeth, and/or to add structural components for increased rigidity. In some embodiments, enlarging or thickening the gingiva may be done to ensure portions (e.g., the anchor) of the fabricated appliance, which is based in part on the FTA digital model, does not engage or contact the patient's gingiva when the appliance is installed. As a result, modifying the FTA digital model as described herein may be done to provide a less painful teeth repositioning experience for the patient.

The process 300 continues at block 308 with obtaining an appliance digital model. As used herein, the term "digital model" and "model" are intended to refer to a virtual representation of an object or collection of objects. For example, the term "appliance digital model" refers to the virtual representation of the structure and geometry of the appliance, including its individual components (e.g., the anchor, arms, biasing portions, attachment portions, etc.). In some embodiments, a substantially planar digital model of the appliance is generated based at least in part on the heat treatment fixture digital model (and/or the FTA digital model). According to some examples, a contoured or 3D appliance digital model generally corresponding to the FTA can first be generated that conforms to the surface and attachment features of the heat treatment fixture digital model. In some embodiments, the 3D appliance digital model can include generic arm portions and securing members, without particular geometries, dimensions, or other properties of the arms being selected or defined by a particular patient. The 3D appliance digital model may then be flattened to generate a substantially planar or substantially 2D appliance digital model. In some embodiments, the particular configuration of the arms 130 (e.g., the geometry of biasing portions 150, the position along the anchor 120 (FIG. 1B), etc.) can then be selected so as to apply the desired force to urge the corresponding tooth (to which the arm 130 is attached) from its OTA toward its FTA. As noted previously, in some embodiments the arms are configured so as to be substantially at rest or in a substantially unstressed state when at the FTA. The selected arm configurations can then be substituted or otherwise incorporated into the planar appliance digital model.

At block 310, the heat treatment fixture can be fabricated. For example, using the heat treatment fixture digital model (block 306), the heat treatment fixture can be cast, molded, 3D printed, or otherwise fabricated using suitable materials configured to withstand heating for shape setting of an appliance thereon.

At block 312, the appliance can be fabricated. In some embodiments, fabricating the appliance includes first fabricating the appliance in a planar configuration based on the planar appliance digital model. For example, the planar appliance can be cut out of a sheet of metal or other suitable material. In some embodiments, the appliance is cut out of a sheet of Nitinol or other metal using laser cutting, water jet, stamping, chemical etching, machining, or other suitable technique. The thickness of the material can be varied across the appliance, for example by electropolishing, etching, grinding, depositing, or otherwise manipulating the material of the appliance to achieve the desired material properties.

According to some examples, the planar member (e.g., as cut out from a sheet of metal) can be bent or otherwise manipulated into the desired arrangement (e.g., substantially corresponding to the FTA) to form a contoured appliance. In some embodiments, the planar appliance can be bent into position by coupling the planar appliance to the heat treatment fixture fabricated at block 310. For example, the arms of the appliance can be removably coupled to hook members of the heat treatment fixture, and optionally ligature wire or other temporary fasteners can be used to secure the arms or other portions of the appliance to the heat treatment fixture. The resulting assembly (i.e., the appliance fastened to the heat treatment fixture) can then be heated to shape-set the appliance into its final form, which can correspond or substantially correspond to the FTA. As a result, the appliance is configured to be in an unstressed, or nearly unstressed, state in the FTA. In operation, the appliance can then be installed in the patient's mouth (e.g., by bending or otherwise manipulating arms of the appliance to be coupled to brackets of the patient's teeth while in the OTA). Due to the shape set of the appliance and the geometry of the arms and anchor, the arms will tend to urge each tooth away from its OTA and toward the FTA.

Additional details and further examples of processes for designing and fabricating appliances and heat treatment fixtures are described below. The particular processes disclosed herein are exemplary, and may be modified as needed to achieve the desired outcome (e.g., the desired force applied to each tooth by the appliance, the desired material properties of the final appliance, etc.). Moreover, although various aspects of the methods disclosed herein refer to sequences of steps, in various embodiments the steps can be performed in different orders, two or more steps can be combined together, certain steps may be omitted, and additional steps not expressly discussed can be included in the process as desired.

Figure 4:
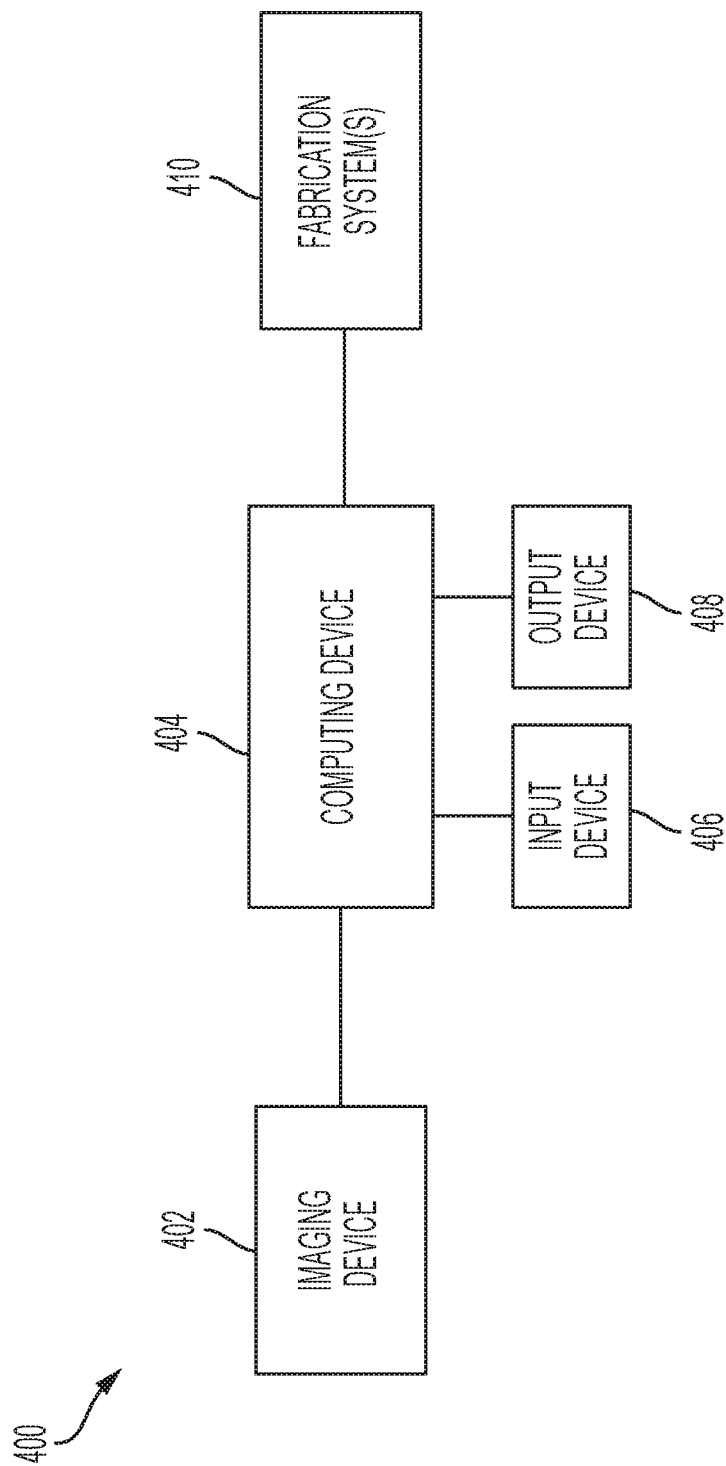
FIG. 4 is a schematic block diagram of a system for manufacturing an orthodontic appliance in accordance with the present technology.

Several of the methods disclosed herein can be performed using one or more aspects of a manufacturing system 400 shown schematically in FIG. 4. The system 400 can include an imaging device 402 communicatively coupled to a computing device 404. The imaging device 402 can include any suitable device or collection of devices configured to obtain image data or other digital representation of a patient's teeth, gingiva, and other dental anatomy. For example, the imaging device 402 can include an optical scanning device (e.g., as commercially sold by ITERO, 3SHAPE, and others), a cone-beam computed tomography scanner, or any other suitable imaging device. In some embodiments, the imaging device 402 can be any suitable device for obtaining a digital representation of a patient's anatomy (e.g., the OTA), even if such digital representation is not based on and does not result in a graphical representation of the patient's anatomy.

The computing device 404 can be any suitable combination of software and hardware. For example, the computing device 404 can include a special purpose computer or data processor that is specifically programmed, configured, or constructed to perform one or more of the computer-executable instructions explained in detail herein. Additionally or alternatively, the computing device 404 can include a distributed computing environment in which tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

The system 400 can also include one or more input devices 406 (e.g., touch screen, keyboard, mouse, microphone, camera, etc.) and one or more output devices 408 (e.g., display, speaker, etc.) coupled to the computing device 404. In operation, a user can provide instructions to the computing device 404 and receive output from the computing device 404 via the input and output devices 406 and 408.

As shown in FIG. 4, the computing device 404 may be connected to one or more fabricating systems 410 (including fabricating machines) for fabricating appliances, heat treatment fixtures, and any other components thereof and associated tools, as described herein. The computing device 404 can be connected to the fabricating system(s) 410 by any suitable communication connection including, but not limited to a direct electronic connection, network connection, or the like. Alternatively, or in addition, the connection may be provided by delivery to the fabricating system 410 of a physical, non-transient storage medium on which data from the computing device 404 has been stored.

Methods of Designing Orthodontic Appliances and Fixtures

Figure 5:
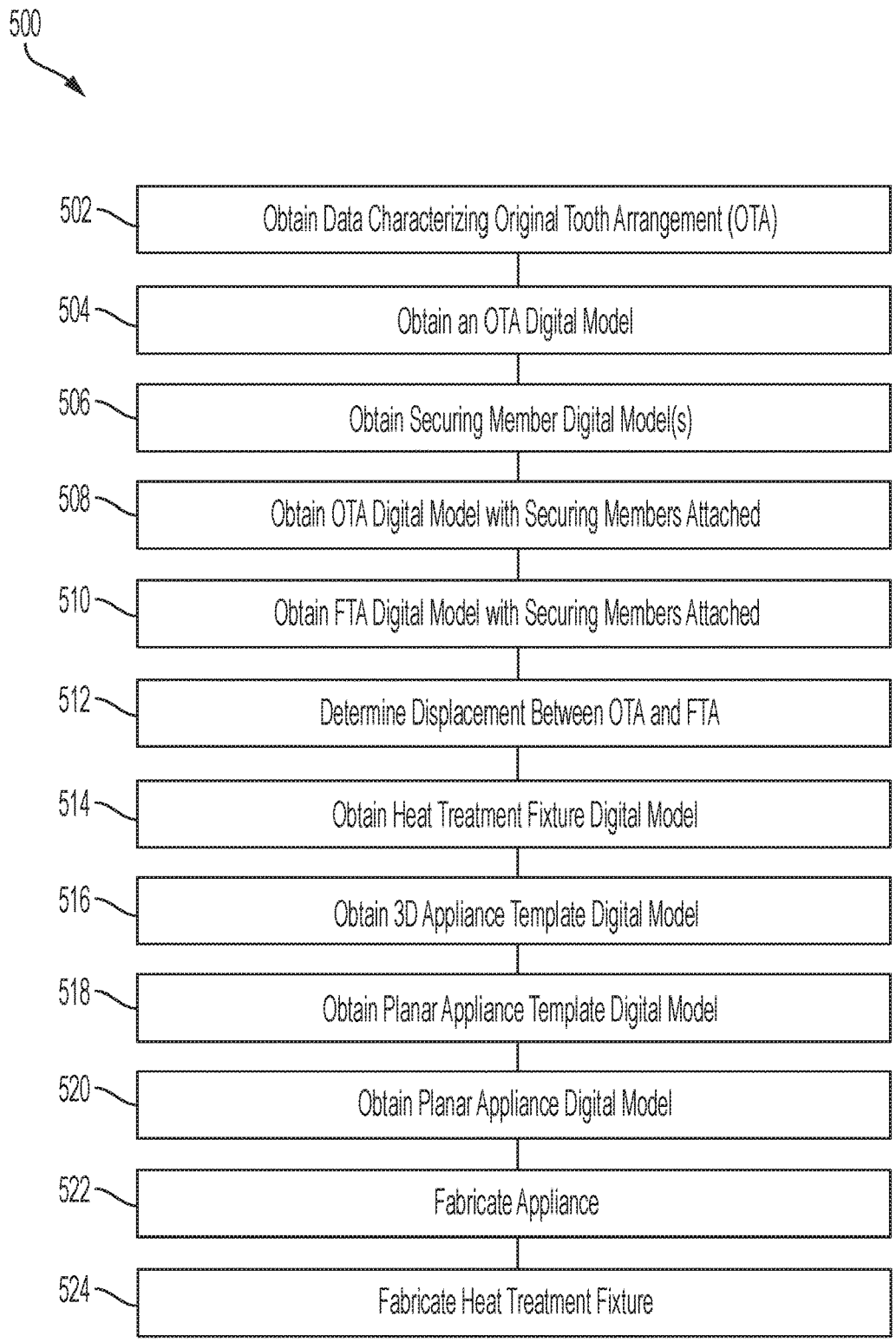
FIG. 5 is a flow diagram of a process for designing an orthodontic appliance in accordance with the present technology.
Figure 6:
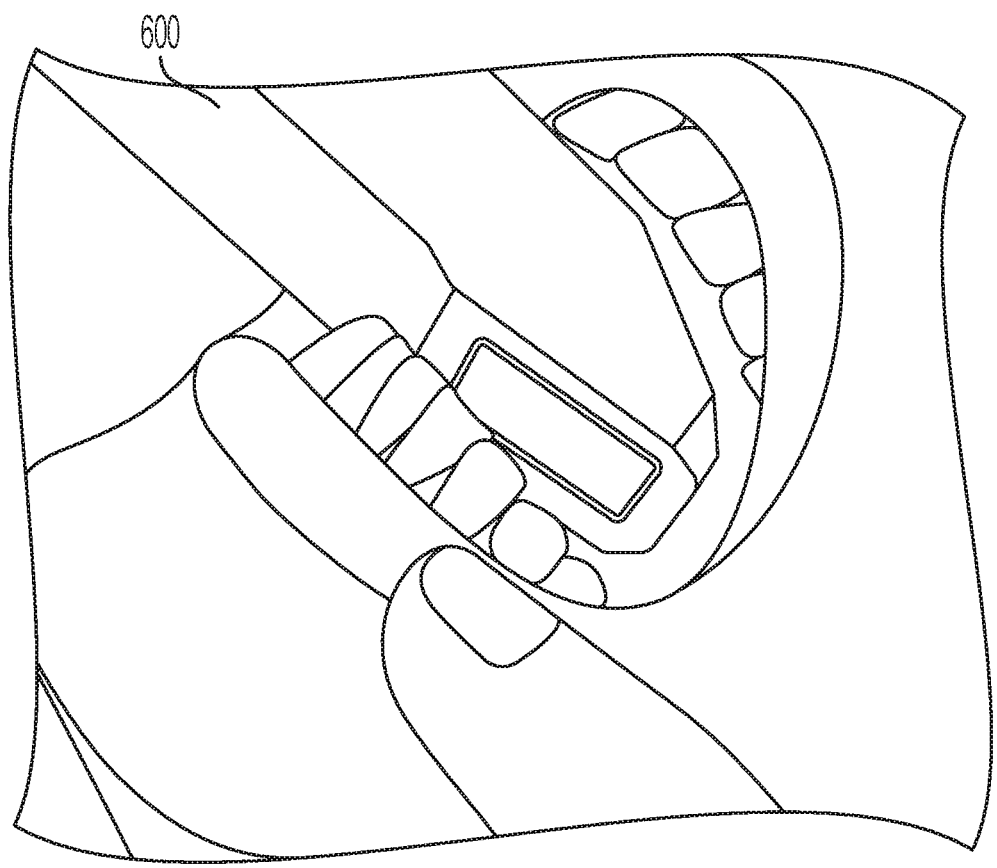
FIG. 6 illustrates scanning a patient's teeth to obtain original tooth arrangement data.

FIG. 5 is a flow diagram of a process 500 for designing an orthodontic appliance. The process 500 begins at block 502 with obtaining data characterizing an original tooth arrangement (OTA). For example, as shown in FIG. 6, the OTA data can be obtained by scanning the patient's teeth using an intraoral optical scanner 600. Such a scanner 600 can be used to scan both the patient's upper and lower teeth to generate a 3D model of each. The scanning can be performed using any suitable technique, for example a dental cone beam CT scanner, or magnetic resonance imaging (MRI), or similar device or technique. In various examples, the OTA data can include data associated with the roots of the teeth as well as the exposed portions, which may be advantageous in designing an appropriate orthodontic appliance. In some examples, the OTA data can be obtained using an impression made of the patient's upper and lower jaws (e.g., using polyvinyl siloxane or any other suitable impression material). The impression can then be scanned to create 3D data, which can include the relationship between the upper and lower jaw (e.g., to record the patient's bite). In examples in which impressions are used, the relationship between the teeth in the upper and lower arches (inter-arch relationship) can be obtained by taking a wax bite of the patient in the centric position. In various embodiments, the OTA data can be obtained directly (e.g., by imaging the patient's mouth using an appropriate imaging device) or indirectly (e.g., by receiving pre-existing OTA data from an operator or another source).

Figure 7:
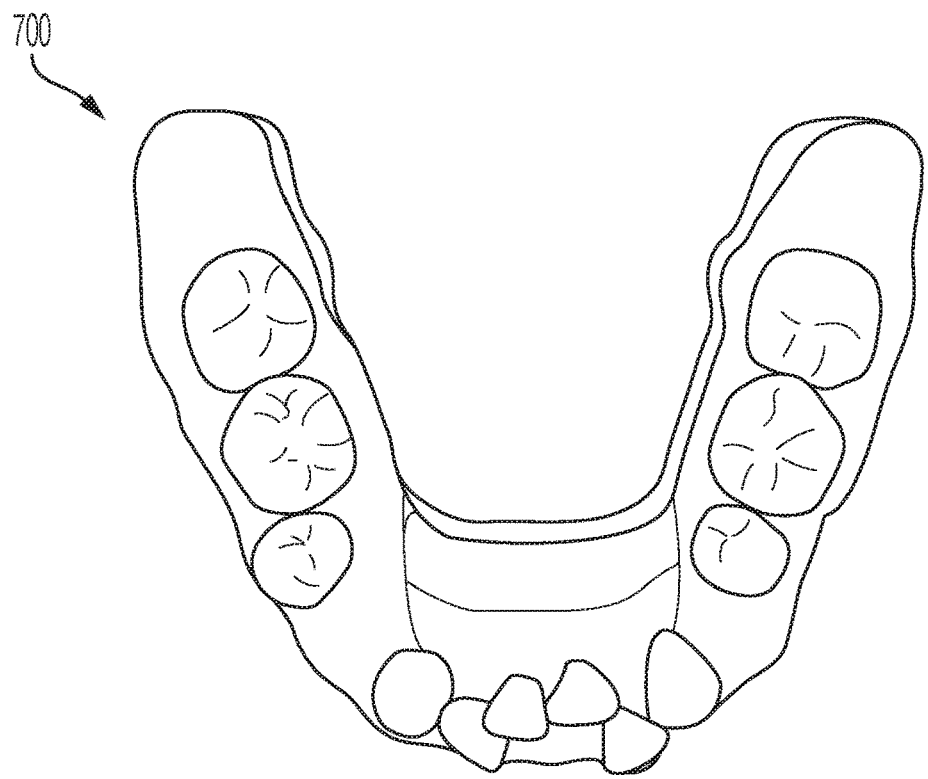
FIG. 7 illustrates an example of a digital model of a patient's teeth and gingiva in an original tooth arrangement.

Returning to FIG. 5, the process 500 continues with obtaining an OTA digital model at block 504. FIG. 7 is a graphical representation of an example of an OTA digital model 700. The digital model 700 can virtually represent or characterize the arrangement of the patient's teeth and gingiva in the original tooth arrangement. As seen in FIG. 7, the teeth in the OTA may be maloccluded, mis-aligned, crowded, or otherwise in need of orthodontic correction. In some embodiments, one or more teeth present in the OTA may be designated for extraction prior to use of the orthodontic appliance.

Figure 8:
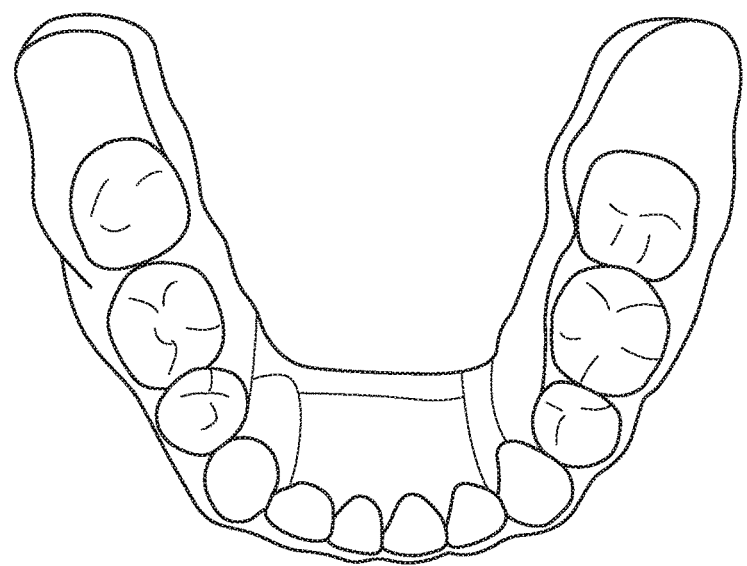
FIG. 8 illustrates an example of a digital model of a patient's teeth and gingiva in a final tooth arrangement.

In some embodiments, obtaining the OTA digital model corresponding to the OTA data can include first obtaining a single complex 3D database of the patient's jaw, which is then segmented to separate the patient's teeth into separate 3D bodies (e.g., individual teeth or blocks of multiple teeth) that can then be manipulated virtually by an operator. Such segmentation can be performed using any suitable techniques or software, for example using iROK Digital Dentistry Studio or other suitable software. Following segmentation, the resulting 3D databases upper and lower teeth can include a model of the gingiva and independent models of each tooth. As a result, the OTA data can be manipulated by an operator to virtually move teeth relative to the gingiva. As described in more detail elsewhere herein, the teeth can be manipulated from the OTA towards a final tooth arrangement (FTA). FIG. 8 illustrates an example final tooth arrangement (FTA). As seen in FIG. 8, the teeth in the FTA may be more aligned, less mal-occluded, and otherwise aesthetically and functionally improved relative to the OTA (e.g., as reflected in the digital model 700). In some embodiments, the FTA can have desired or favorable inter-arch and intra-arch arrangements, for example, based on an operator's prescription. For example, one or more (or all) teeth from the upper or lower jaws (or both) are moved until their cusps have a good interdigitation and fit.

Figure 9:
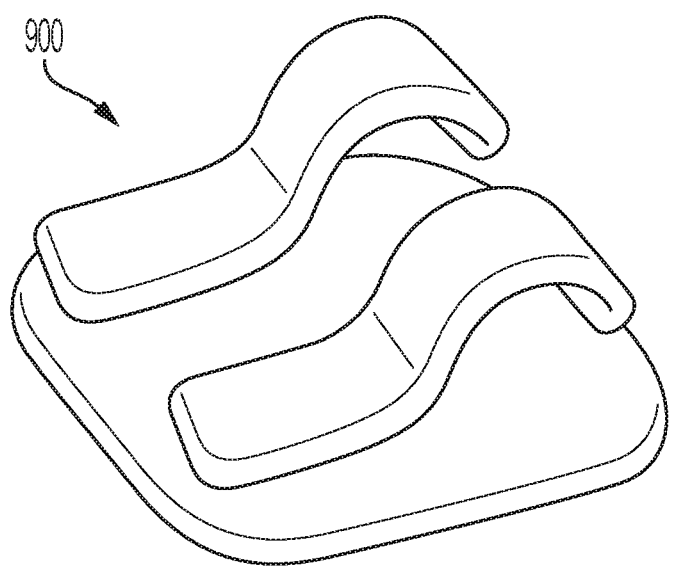
FIG. 9 illustrates an example of a digital model of a securing member.

Referring back to FIG. 5, the process 500 continues in block 506 with obtaining securing member digital model(s). As discussed previously, securing members (e.g., securing members 160, brackets, etc.) can be coupled to the patient's teeth to allow for an orthodontic appliance (e.g., appliance 10) to be mated thereto. The securing member digital models can include virtual representation of the geometry and/or other structural characteristics of the securing member(s). In various embodiments, the securing member digital models can be identical for each securing member, or may vary among the securing members. For example, different securing members may be used for molars than for incisors. FIG. 9 illustrates an example securing member digital model 900.

Figure 10:
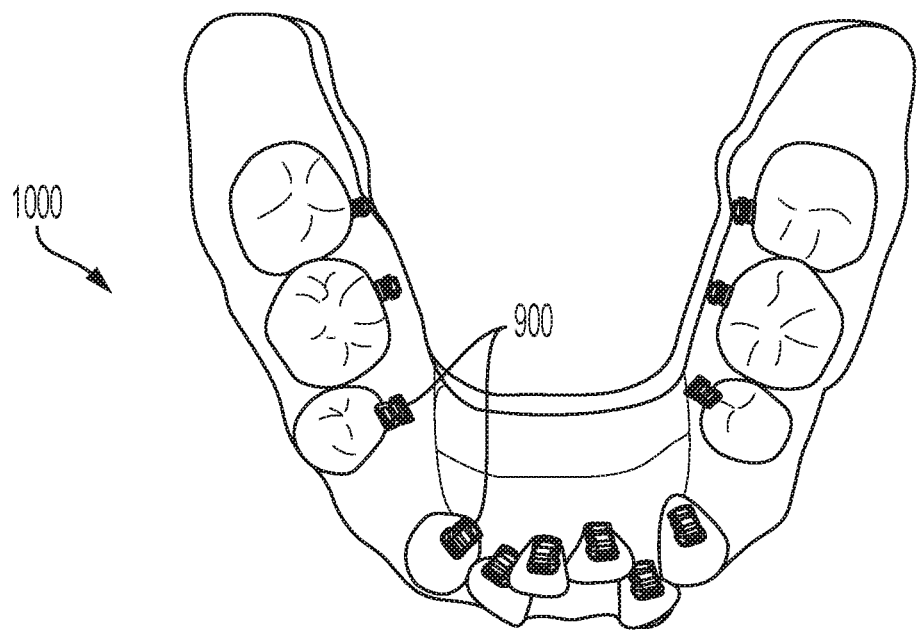
FIG. 10 illustrates an example of a digital model of a patient's teeth and gingiva and a plurality of securing members in an original tooth arrangement.

With continued reference to FIG. 5, the process 500 continues in block 508 with obtaining an OTA digital model with securing members attached. For example, the securing member digital model 900 (FIG. 9) can be applied to appropriate locations on the patient's teeth within the OTA digital model 700 (FIG. 7). The resulting digital model 1000 is shown in FIG. 10, in which a plurality of digital models of securing members 900 are disposed along lingual surfaces of the patient's teeth. In some embodiments, in the digital model 1000, each of the patient's teeth can have a securing member coupled thereto. As noted previously, an orthodontic appliance can include a plurality of arms having attachment portions configured to be coupled to securing members (e.g., brackets) that are attached to the patient's teeth.

In some examples, the digital models 900 of the securing members can be virtually positioned on the teeth in the OTA using appropriate software (e.g., iROK Digital Dentistry Studio). In some embodiments, virtually positioning the securing members can include selecting virtual models of particular securing members from a library of available securing members, and then positioning the selected securing members on one or more teeth. In some embodiments, the bracket positioning can be assigned automatically (e.g., by automatically positioning the bracket in a central or the pre-defined portion of the tooth) or manually (e.g., by an operator selecting and/or manipulating the attachment location for each securing member). In some embodiments, the position of each securing member can be refined by the operator as desired. For example, it may be desirable to position the securing members as close to the gingiva as possible so as to avoid interference with securing members on the other jaw or interference with the teeth from the other jaw when the mouth is closed.

In some embodiments, the digital model 1000 with the teeth in the OTA and securing members attached thereto can be used to determine a configuration of a bonding tray, which may then be used to physically attach securing members to the patient's teeth by an operator. For example, the bonding tray can be configured to fit over the patient's teeth similar to an aligner, and can include recesses on a side of each tooth that are sized and configured to receive an appropriate securing member (e.g., bracket) therein. In various embodiments, such recesses can be positioned on the lingual, buccal, mesial/distal, occlusal, root, or any suitable surface of a tooth to which a corresponding bracket is intended to be bonded. In operation, an appropriate securing member can be placed in each recess and then an adhesive (e.g., an adhesive that cures when illuminated by ultraviolet light) can be applied to the bonding surface of each securing member. The tray can then be placed over the patient's teeth and the adhesive cured to bond all the securing members to the appropriate location on each tooth.

To generate such a bonding tray, the digital model 1000 can be used, which characterizes the teeth in the OTA with securing members attached. The digital model 1000 may be further manipulated, for example, to remove excess virtual gingiva to limit the size of the tray to only what is necessary to hold the securing members in position against the patient's teeth. The trimmed digital model can then be used to generate a physical 3D model of the patient's teeth with the securing members disposed thereon, for example using 3D printing in a polymer resin or other suitable technique.

In some embodiments, A suitable material (e.g., a clear polymer resin) can then be formed over (e.g., thermoformed over) the physical model of the patient's teeth with securing members in the OTA. This can create the aligner-like tray with recesses shaped and configured to receive securing members therein. The securing members can then be placed into corresponding recesses of the tray, and the tray can be applied to the patient's teeth with a curable adhesive to attach the securing members to the patient's teeth in the OTA. The tray may then be removed, leaving the securing members in place.

In some embodiments, the bonding tray can be 3D printed directly, without the need for a physical model of the patient's teeth and without the use of thermoforming. For example, a digital model of a bonding tray can be derived from the digital model 1000 characterizing the teeth in the OTA with securing members attached. In some embodiments, a negative of the digital model 1000 can be generated, and can be trimmed to provide a general tray-like structure with a surface corresponding to the teeth and securing members in the digital model 1000. This resulting model can be manipulated to provide features for retaining brackets in the corresponding recesses. Finally, the bonding tray can be 3D printed based on this digital model, for example using 3D printable polymer resins or other suitable materials or deposition techniques.

Alternatively, the operator may attach securing members to the patient's teeth directly, without the assistance of a tray.

Figure 11:
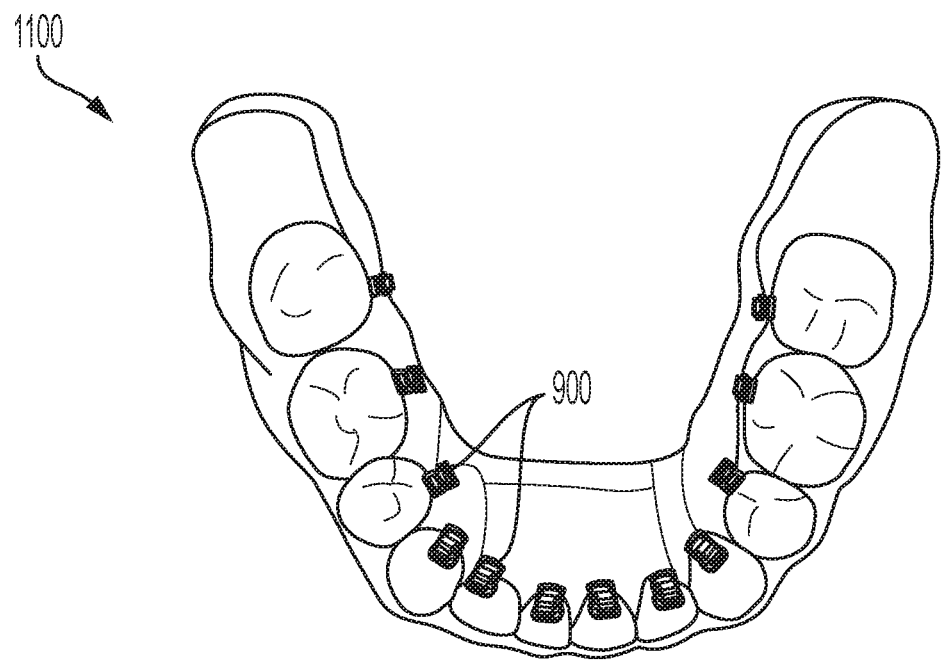
FIG. 11 illustrates an example of a digital model of a patient's teeth and gingiva and a plurality of securing members in a final tooth arrangement.

Referring back to FIG. 5, the process 500 continues at block 510 with obtaining an FTA digital model 1100 (FIG. 11) with securing members 900 attached. For example, the digital model 1000 (FIG. 10) of the teeth in OTA with models of the securing members 900 attached thereto can be used to generate the FTA digital model 1100 (FIG. 11). In some embodiments, the digital model 1000 can be manipulated to place the teeth in the FTA.

The FTA digital model 1100 can be derived based at least in part on data characterizing the teeth in the FTA. Such FTA data can include a digital representation of the desired final positions and orientations of the patient's teeth relative to one another and to the gingiva. The FTA data can be obtained directly (e.g., generated by the operator) or may be received from an external source (e.g., the FTA data may be generated by a third party and provided to an operator for design of an appropriate orthodontic appliance).

In some embodiments, the FTA data can be obtained by manipulating the OTA data to virtually move the patient's teeth. Suitable software, such as iROK Digital Dentistry Studio, can be used by an operator to move the teeth to a desired FTA. In some embodiments, virtual movement of the teeth relative to the OTA also results in movement of the gingiva relative to the OTA in order to maintain the natural look of the gingiva and more accurately reflect the orientation and position of the gingiva when the teeth are at the FTA. This movement of the gingiva can be achieved using gingiva morphing or other suitable technique.

In some embodiments, the FTA can reflect changes to the patient's teeth that may occur as part of the treatment process. For example, an operator may extract one or more teeth of the patient, due to lack of space for all the teeth to fit in the arch (or other reasons), as part of the treatment. In that event, the extracted teeth can be excluded from the FTA data. If the operator decides that the teeth need to become smaller due to a lack of space, then interproximal reduction (IPR) may be performed on the patient. In this case, stripping and reducing the size of the teeth in the FTA can be performed so as to match the IPR done by the operator.

In some embodiments, a proposed FTA can be developed by an operator (e.g., independently or based in whole or in part on input from a treating orthodontist) and then sent to a treating orthodontist for review and comment. If the treating orthodontist has comments, she can provide input to the operator (e.g., written notes, proposed manipulation of one or more teeth or securing members, etc.) that can be transmitted electronically or otherwise. The operator may then revise the FTA and send a revised proposed FTA back to the treating orthodontist for further review and comment. This iterative process may repeat until the treating orthodontist approves the proposed FTA, and the resulting digital model 1100.

Additionally or alternatively, an FTA digital model (e.g., as depicted in FIG. 8) can be manipulated to have digital models of securing members 900 coupled to the teeth at appropriate locations. In some embodiments, the relative position of each securing member relative to its respective tooth may be obtained or derived from the digital model 1000 (FIG. 10), in which the securing members are attached to the teeth in the OTA. In some embodiments, the securing members may be first positioned on the teeth in the FTA to generate the digital model 1100 (FIG. 11), and this model may in turn be used to generate the digital model 1000 (FIG. 10), for example by manipulating the digital model 1100 to move the teeth to the OTA.

Referring back to FIG. 5, the process 500 continues at block 512 with determining the displacements of individual teeth or groups or teeth between the OTA and the FTA. For example, the displacement of each tooth between the OTA and FTA can be described using six degrees of freedom (e.g., translation along X, Y, and Z axes, and rotation around the same three axes; or alternatively translation along mesiodistal, buccolingual, and/or occlusogingival directions, and rotation in the form of buccolingual root torque, mesiodistal angulation, and/or mesial out-in rotation). In some embodiments, these values can be determined by calculating the difference between the location of each tooth in the FTA data and the OTA data. This can be performed for each tooth in each jaw to generate a dataset that includes the required displacement along six degrees of freedom for each tooth.

Figure 12:
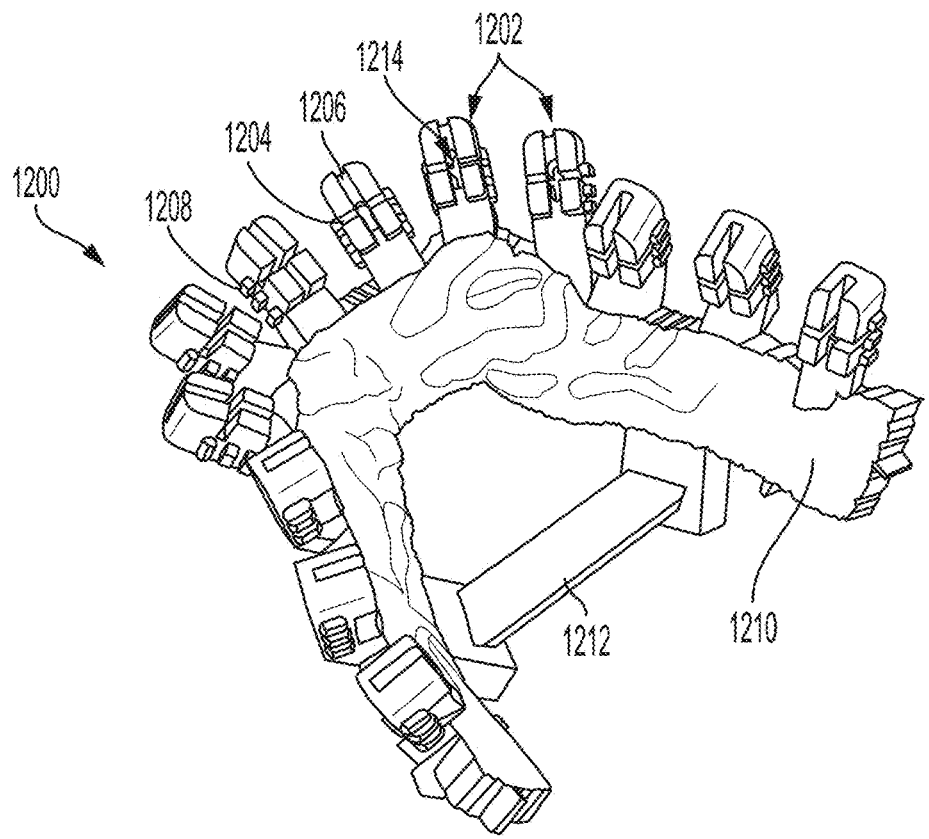
FIG. 12 illustrates an example of a digital model of a heat treatment fixture.

The process 500 continues at block 514 with obtaining a heat treatment fixture digital model. FIG. 12 illustrates an example fixture digital model 1200, which can be generated by manipulating the digital model 1100 (FIG. 11) of the FTA with securing members attached. For example, the digital model 1100 can be manipulated to generate a digital representation of a fixture (e.g., a heat treatment fixture) for use in manufacturing an appliance. The digital model 1100 can be manipulated in a number of ways to generate suitable fixture data. In some embodiments, such manipulation can be performed using suitable software, e.g. MeshMixer by Audodesk®.

In some examples, the securing members in the digital model 1100 can be modified or substituted with appropriate securing portions 1202 that are each configured to couple to arms of an appliance and to facilitate temporary fastening of the appliance to the fixture. For example, bracket-like securing members can be replaced with securing portions 1202 that include both horizontal channels 1204 configured to mate with attachment portions 140 of an appliance 100 as well as vertical channels 1206. A plurality of protrusions 1208 can be disposed along one or more side surfaces of the securing portions 1202. Together, the channels 1204 and 1206 and the protrusions 1208 can provide structures that are configured to receive ligature wire or other fastener therethrough. For example, an operator can couple an appliance 100 to the fixture and then wind ligature wire through the horizontal channels 1204 and within the space between adjacent protrusions 1208 to hold the appliance 100 in place against the fixture. Additionally or alternatively, the horizontal channels 1204 can be configured to mate with attachment portions 140 of the appliance 100, for example being sufficiently deep (e.g., deeper than corresponding channels of the securing members 900 of the digital model 1100) to both receive the attachment portions 140 therein and to receive ligature wire or other fastener therethrough. In some embodiments, the vertical channels 1206 can be configured to mate with part of the attachment portions 140 of the appliance 100, such that a single attachment portion 140 can be partially received within a horizontal channel 1204 and partially received within a vertical channel 1206. The protrusions 1208 may additionally define grooves or recesses configured to receive the ligature wire or other elongate fastener. The fixture model 1200 can also define throughchannels or apertures 1214 within each securing portion 1202. These through-channels 1214 can allow a pushing tool to be inserted from the back of the securing portion 1202 (e.g., through the buccal surface of the fixture model 1200) to push an attachment portion 40 away from the securing portion 1202 after the heat treatment has been completed and the ligature wire or other fastener has been removed.

Additionally or alternatively, the digital model 1100 can be manipulated to alter the shape or configuration of the gingiva to generate the fixture model 1200. When an appliance is installed, a patient may suffer considerable discomfort if any portion of the appliance impinges on the gingiva. Accordingly, it can be desirable to design an appliance that rests close to the patient's gingiva without impinging upon it. In some embodiments, this can be achieved by enlarging the gingiva of the digital model 1100 to generate the fixture model 1200. For example, the lingual surface of the gingiva in the digital model 1100 can be expanded (e.g., moved more lingually) by a predetermined amount (e.g., less than about 1.5 mm, less than about 1.4 mm, less than about 1.3 mm, less than about 1.2 mm, less than about 1.1 mm, less than about 1.0 mm, less than about 0.9 mm, less than about 0.8 mm, less than about 0.7 mm, less than about 0.6 mm, less than about 0.5 mm, less than about 0.4 mess, less than about 0.3 mm, less than about 0.2 mm, or less than about 0.1 mm). As such, when an appliance is generated using the surface of the fixture data (e.g., the appliance 100 can be shaped to substantially correspond to a portion of the lingual surface of the fixture model 1100, as described in more detail below), the appliance can be sized and configured to rest a short distance away from the patient's gingiva without impinging thereon.

With continued reference to block 514, the digital model 1100 with securing members attached can be manipulated to remove the teeth or other structural elements not needed for heat treating the appliance, and/or to add structural features to reinforce the fixture for sufficient rigidity during the heat treatment process. For example, as shown in FIG. 12, the fixture model 1200 does not include any teeth, but retains at least a portion of the gingival surface 1210. Additionally, the fixture model 1200 includes a stabilizing crossbar 1212 that can enhance the rigidity of the resulting fixture. Various other modifications to the digital model 1100 can be made to achieve the desired heat treatment fixture model 1200.

Figure 13:
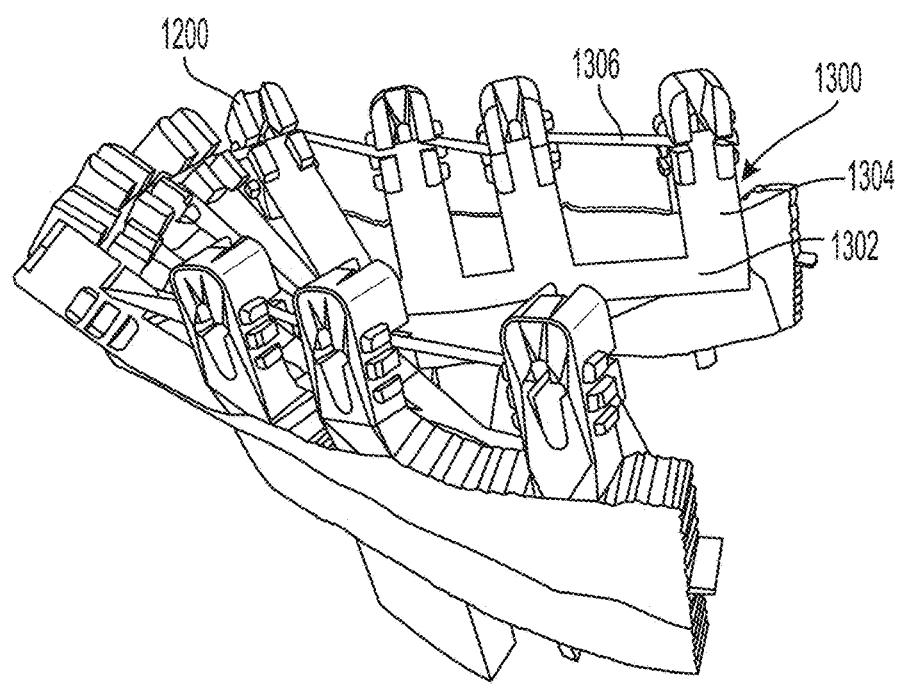
FIG. 13 illustrates an example of a digital model of a three-dimensional appliance template that is based on the heat treatment fixture model.

Referring back to FIG. 5, the process 500 continues at block 516 with obtaining an appliance template digital model. FIG. 13 illustrates an example of an appliance template digital model 1300, shown here in a configuration mated with the fixture model 1200.

The model 1300 defines an anchor portion 1302, arm portions 1304, and an attachment bar portion 1306. These components can take the form of a genericized template for an appliance that is later customized for a particular patient (as described in more detail below with respect to FIG. 15). For example, the anchor portion 1302 can correspond to the anchor 120 of the completed appliance, and the arm portions 1304 can serve as placeholders for the arms 130 of the completed appliance. The attachment bar portion 1306 takes the form of a continuous strip connecting each of the arms 130. As shown in FIG. 13, the arm portion 1306 can be configured to be received within the channels 1204 of the securing portions 1202 of the fixture model 1200. The attachment bar portion 1306 can correspond in part to portions of the attachment portions 140 of the arms 130 of the completed appliance.

In various embodiments, the appliance template digital model 1300 can be generated using surface data of the fixture model 1200. For example, the appliance template digital model 1300 can be configured to substantially correspond to the surface of the fixture model 1200, such as the anchor portion 1302 corresponding to a contour of the fixture model 1200 that is derived from data characterizing the patient's gingiva. As noted previously, the treatment fixture model 1200 can be modified with respect to the OTA model 1100 by, among other things, enlarging the gingiva. As such, when the anchor portion 1302 contacts the gingival portion of the fixture model 1200, the anchor portion 1302 may be positioned so as to be slightly spaced apart from the actual gingiva as characterized in the OTA model 700. In some embodiments, the appliance template model 1300 can have no thickness dimension, instead corresponding to a three-dimensional surface following a contour of the fixture model 1200. In some embodiments, the appliance template model 1300 can have at least some thickness.

Figure 14:
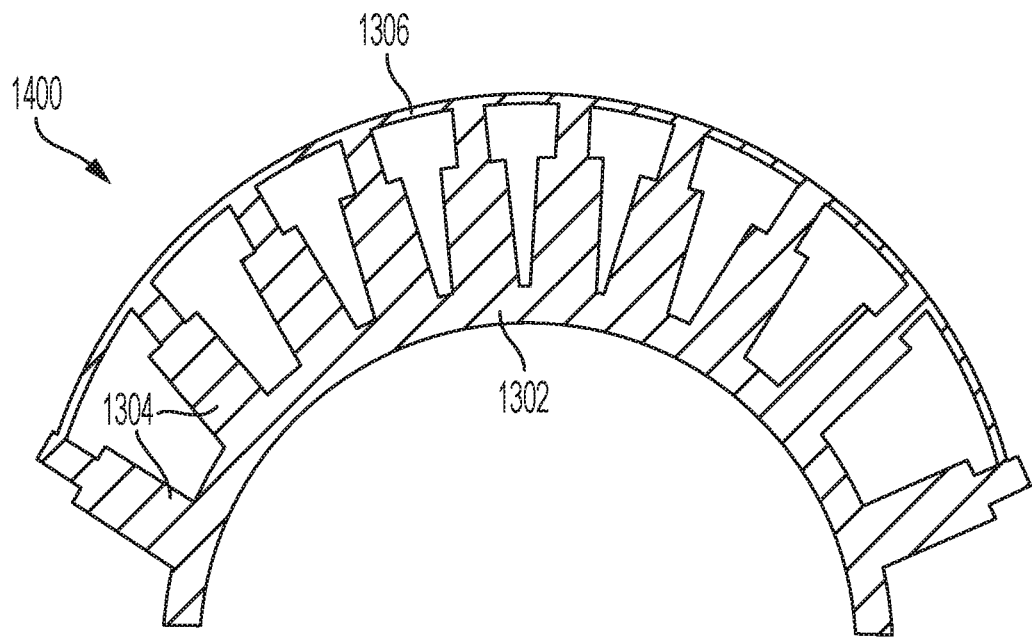
FIG. 14 illustrates an example of a digital model of a substantially planar appliance template.

In block 518, the appliance template digital model 1300 can be flattened or otherwise manipulated to generate a planar appliance template model 1400 (FIG. 14). The planar template model 1400 can reflect 2-dimensional or substantially planar data corresponding to or at least derived from the contoured appliance template model 1300. For example, the appliance template digital model 1300 (FIG. 13) can be converted into the planar appliance template model 1400 (FIG. 14) by flattening, planarizing, or otherwise converting the digital model 1300 to generate the planar appliance template model 1400. Such conversion may be carried out using a processor system and appropriate software such as, but not limited to ExactFlat®, Solidworks®, Autodesk® Inventor, Creo®, or other suitable software.

Figure 15:
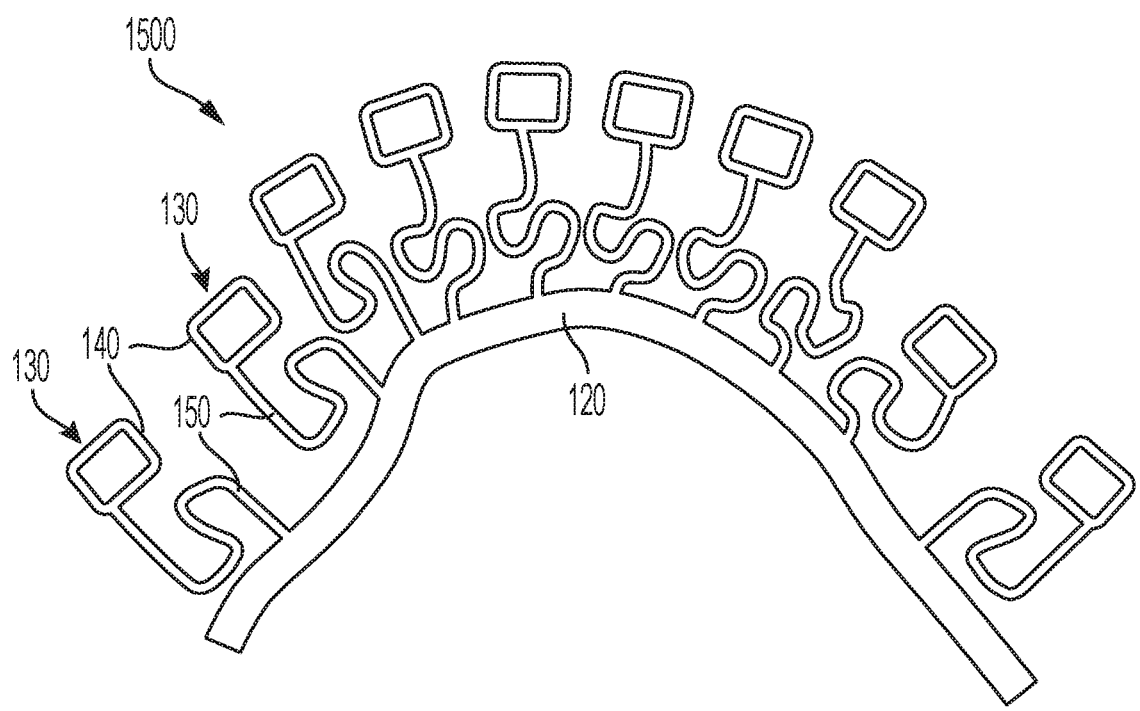
FIG. 15 illustrates an example of a digital model of a substantially planar appliance with unique arm geometry based on determined displacement of each tooth.

At block 520, the planar appliance digital model is obtained. An example of a planar appliance model 1500 is shown in FIG. 15. In this stage, the particular shape and configuration of the arms of the appliance can be determined, such as by modifying or substituting portions or components of the planar template model 1400 (FIG. 14). For example, the particular dimensions, geometry, and material properties of arms of the appliance can be selected so as to apply the necessary force and/or torque to achieve the desired displacement determined at block 512. In some embodiments, a pre-populated library of arm designs can be used to select an appropriate design and configuration to achieve the desired displacement. In some embodiments, the arm designs in the pre-populated library can be analyzed using finite element analysis (FEA) or other techniques to determine the spring force such arms would apply when deflected by particular amounts (e.g., the amount of deflection between the FTA (when the arm is at rest) and the OTA). In some embodiments, fully or partially automated selection of particular arm designs can be reviewed and/or modified by an operator based on relevant criteria. For example, if the proposed arm designs include overlapping or otherwise interfering arms, the operator may manually adjust the shape and/or configuration of the arms.

Based on the determined displacement, the required forces and/or torques required to move each tooth from the OTA to the FTA can be determined. The forces required to move teeth are generally in the range of centiNewtons, and distances moved are typically in the range of millimeters. The amount of moment (Newton-millimeter) acting to rotate a tooth can be found by multiplying the magnitude of the applied force by the force arm. In general, the displacement can be a 3D tooth movement that combines both translational and rotational motion.

The forces and/or torques required to achieve the FTA may depend on the patient's anatomy, for example the size of the particular tooth being moved, the anatomy of the root, etc. The forces and/or torques may also depend on other physiological parameters (e.g., bone density, biological determinants, sex, ethnicity, jaw (maxilla or mandible), mechanical properties of surrounding tissues (lips, tongue, gingiva, and bone) around the moving tooth, etc.). The particular force and/or torque applied to a given tooth will also depend on the particular positioning of the securing member (e.g., bracket). For example, a securing member positioned further off a center-of-resistance of a tooth will generate more torque under a given applied force than a securing member that is positioned nearer to a center-of-resistance of the tooth. Based on the desired displacement (e.g., along six degrees of freedom), the patient's anatomy, and the location of the securing member, a particular arm configuration can be selected to generate the desired force and/or torque on the subject tooth, so as to move the tooth from the OTA to the FTA. By determining appropriate thickness, widths, shapes, and configurations of the arms and other components of the orthodontic appliance, an appliance configuration that applies forces and torques to the appropriate teeth to move the teeth to the FTA is determined.

In particular examples, the design of the appliance may be performed by an operator, with the processor system and appropriate design software such as, but not limited to CAD software such as, but not limited to Solidworks®, Autodesk® Inventor, Creo®, or the like. FEA software such as, but not limited to Abaqus, Ansys, etc. may be employed to design the springs and arms in order to apply the desired or optimal force to the teeth. For example, such software and processing systems may be employed to design and alter the thickness, cut width, length, as well as the overall design of each arm based at least in part on the movement of the tooth to which the arm is connected.

In some examples, if a tooth needs to be displaced by a longer distance or the tooth is smaller (e.g. lower incisors), the arm 130 may be designed such that it is more flexible. In some embodiments, the selection or design of the arms 130 can account for variation in the rate of teeth movement based on direction. It is known that the rate of tooth movement when a given force is applied to the tooth is different depending on the direction of movement. For example, extrusion is the fastest movement for a given force, intrusion is the slowest, and mesiodistal and buccolingual movements are somewhere in between these two extremes. In one example, if a tooth moves 2 mm per month occlusally and 1 mm per month distally under the same applied force, the tooth will not move in a straight line as the occlusal movement will be more rapid than the distal movement. The occlusal movement will finish first, and then the tooth will move in a straight line from there in the distal direction until that motion is complete. It may be desired to move the tooth in a particular trajectory, and so the force applied distally can be different from the force applied occlusally. For example, it may be desired to move the tooth in a straight line, and so the distal force would have to be greater than the occlusal force in order to result in a straight trajectory from OTA to FTA.

In some embodiments, the arms 130 can be designed to impart less force on some or all of the teeth because of periodontal problems such as bone resorption, root resorption or attachment loss. The ability to customize the force or torque (or both) applied to each tooth can provide significant advantages over traditional orthodontics. In particular examples, the computer-aided procedure employs an algorithm for selecting or configuring an arm or other feature of an appliance, for example, from one or more predefined sets of options or one or more ranges of options. Thus, for example, a set of options or a range of options may be predefined for one or more parameters associated with an arm or other feature.

The one or more parameters associated with an arm 130 may include, but are not limited to, the overall length of the arm, the shape or configuration of the biasing portion 150, the shape or configuration of the bracket connector 40, the width dimension of one or more sections of the arm 130, the thickness dimension of one or more sections of the arm 130, or the like.

Obtaining the planar appliance digital model 1500 can also include determining the shape and configuration of the anchor 120. For example, the anchor 120 can be selected so as to substantially conform to the patient's gingiva without impinging thereon. The thickness, depth, or other properties of the anchor 120 can also be selected to provide sufficient rigidity against the forces generated by the arms. In some embodiments, the anchor 120 design can be automatically generated (e.g., by being automatically generated to substantially conform to the patient's gingiva or other location in the FTA model (e.g., model 1100) or the OTA model (e.g., model 700 or 1000). In some embodiments, an operator may manually select or revise the design and configuration of the anchor as desired.

Although in the illustrated embodiment, the specific features of the arms 130 are selected while the appliance model is in a substantially planar or 2D form, in other embodiments the appliance features can be selected and configured based on a digital model that is contoured to correspond to a patient's anatomy. For example, the 3D appliance template model 1300 (FIG. 13) can be modified to select particular arms 130, anchor 120, or any aspects thereof to achieve the desired appliance. In some embodiments, the template is omitted altogether, and a customized appliance model is generated based on the OTA model and/or the FTA model without the use of an intervening template model.

In some embodiments, the planar appliance model 1500 can be 2D, such that the model defines no thickness of the appliance. Such a model can be used, for example, to cut an appliance out of a sheet of material. In such cases, the thickness can be determined by selecting the sheet of material and by polishing, etching, grinding, deposition, or other techniques used to modify a final thickness of the appliance. In some embodiments, the planar appliance model 1500 can define a thickness dimension while remaining substantially planar or flat. For example, the planar appliance model 1500 can define a thickness of the appliance which may be uniform or may vary across some or all of the anchor 120 and arms 130.

In some embodiments, a 3D or contoured appliance model can be generated, for example by manipulating the planar appliance model 1500 into a curved or contoured configuration. In some embodiments, the 3D appliance model can correspond to the appliance mounted to the teeth in the OTA (e.g., by manipulating the planar appliance model 1500 using position data of the securing members 900 in the OTA model 1000 (FIG. 10), or by manipulating the planar appliance model 1500 using position data of the securing members 900 in the FTA model 1100 (FIG. 11)).

With reference to blocks 516, 518, and 520 together, in some examples a computer-aided procedure can be used to select or determine the shape and configuration of the arms, anchor, and/or any other features of an appliance. The procedure may be configured to select one (or more than one) arm, securing member, anchor, or parameter thereof, or any other aspect of the appliance based on one or more input data. For example, input data may include, but is not limited to, a type of a tooth (e.g., molar, canine, incisor, etc.) or a size of a tooth. A larger tooth (such as a molar) may require larger arms or larger, wider or thicker loop or curved features for providing a greater force, than for a smaller tooth (such as an incisor). Additionally or alternatively, input data may include the size of the periodontal ligament (PDL) of one or more teeth. The size of the PDL may be obtained by any suitable process including, but not limited to, CBCT scan or other imaging technique. Other input data may include, but is not limited to, the number or direction of forces to be applied to a tooth or teeth in a three-dimensional space. For example, a desired tooth movement direction may require one or more shapes or configurations of arms that differ from the shapes or configurations required for a different tooth movement direction. Other input data may include but is not limited to, the number or direction of rotational forces (or torque) to be applied to a tooth or teeth. For example, a desired tooth movement in a rotational direction may require one or more shapes or configurations of arms that differ from the shapes or configurations required for a different tooth movement direction. Additionally, in some embodiments two or more arms can be attached to a single tooth, either with each arm coupled to a separate securing member, or with two arms coupled to the same securing member. In such instances, the input data can include a number of arms and/or securing members coupled to each tooth, or alternatively the number of arms and/or securing members can be generated as output data.

In some embodiments, this computer-aided procedure can include an algorithm that includes, as input, (but is not limited to) one or more values representing one or more of: (a) up to three translational and up to three rotational movements from an OTA to an ITA or FTA, or from an ITA to another ITA or FTA; (b) the surface of periodontal ligament (PDL) or the area of the root of a or each tooth; (c) bone density of the patient; (d) biological determinants for example, obtained from saliva, gingival fluid (GCF), blood, urine, mucosa, or other sources; (e) gender of the patient; (f) ethnicity of the patient; (g) the jaw (maxilla or mandible) for which the appliance is to be installed; (i) the number of teeth on which the appliance is to be installed; and (j) mechanical properties of the tissue (lips, tongue, gingiva) and bone around the teeth to be moved. In various embodiments, one or more of such inputs can affect the forces (e.g., magnitude, direction, point of contact) required to move each tooth from the OTA to or toward the FTA.

In other examples, other suitable input data may be employed. The computer-aided process employs a computer programmed or configured with suitable non-transient software, hardware, firmware, or combinations thereof, to generate an output (such as one or more selected arm configurations, anchor configurations, or securing member configurations), based on the one or more input data.

An output generated by the computer-aided procedure, based on such input, can include, but is not limited to one or more of: (a) a design of an arm; (b) a width or cut-width of one or more of such arms; (c) a thickness dimension of any portion of the appliance of the entire appliance; (d) mechanical properties of such arms including but not limited to amount of flexibility, or a magnitude of bias force or resilience; (e) a design of an anchor; (f) a width or thickness of the anchor; (g) connection locations between the arms and the anchor; and/or (h) transformational temperature of the nitinol (or other material) in one or more (or each) section of the appliance. As noted previously, in some embodiments the output can include particular configurations selected from among a pre-populated library of anchors and/or arms. For example, based on the inputs, a desired force (e.g., magnitude and direction) can be determined for each tooth. Based on the desired force, an appropriate anchor member and/or arm configuration can be selected that provides the desired force or a suitable approximation thereof. In some embodiments, the configuration of the appliance (including any of the outputs listed above) can be generated independently of any pre-populated library. In some embodiments, generating the output can include analyzing provisional selections or designs using finite element analysis (FEA) or other techniques to determine performance parameters, for example, the spring force such arms would apply when deflected by particular amounts (e.g., the amount of deflection between the FTA (when the arm is at rest) and the OTA).

In particular examples, computer-aided processes can be employed to make customized appliances, for each given patient. In other examples, appliances may be made in a plurality of predefined sizes, shapes, configurations, or the like, based on a population group. Accordingly, a different semi-customized size, shape or configuration would be configured to fit each different selected portion of the population group. In that manner, a more limited number of different appliance sizes, shapes and configurations may be made to accommodate a relatively large portion of the population.

Based on the determined shape and configuration of the arms and the anchor, the full appliance shape data can be generated. In some embodiments, the appliance shape data can take the form of 3D data (e.g., the appliance in its shape-set form following heat treatment or other suitable setting technique) or planar or substantially 2D data (e.g., the appliance in its laid-flat form, for example as cut out from a sheet of material).

At block 522, an appliance can be fabricated (e.g., based on the planar appliance digital model 1500 (block 520). And at block 524, a heat treatment fixture can be fabricated (e.g., based on the heat treatment fixture digital model 1200 (block 514). Fabrication of the heat treatment fixture and the appliance are described in more detail below.

In some embodiments, generating the full appliance shape data can include obtaining a heat treatment fixture model (e.g., as described below with respect to FIG. 12), and generating a preliminary appliance model based on the heat treatment fixture model. For example, the preliminary appliance model can conform to at least a portion of a lingual surface of the heat treatment fixture model. The preliminary appliance model can then be modified to include the determined arms and anchor, to have a determined thickness profile, etc. The modified appliance model may then be flattened for use in fabrication as described below.

Methods of Fabricating Orthodontic Appliances

Figure 16:
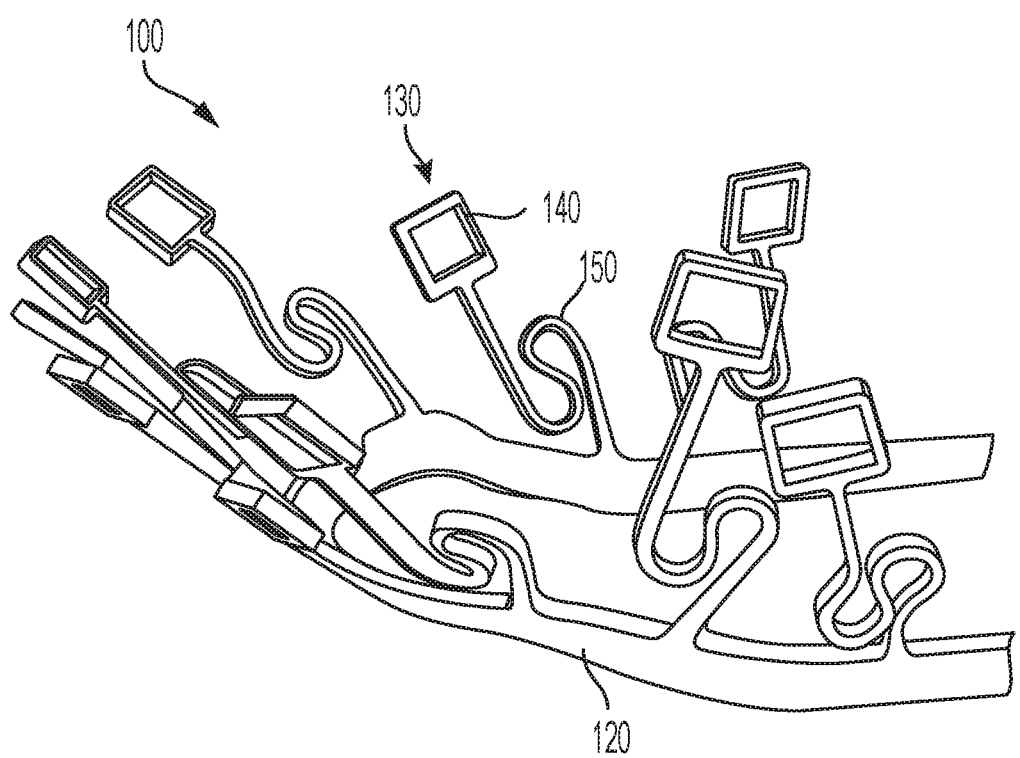
FIG. 16 illustrates a perspective view of an orthodontic appliance in accordance with embodiments of the present technology.

As noted above, one or more digital models can be generated that characterize or define an appliance (e.g., the planar appliance digital model 1500, or a contoured appliance digital model). In various embodiments, one or more such digital models can be used to fabricate an appliance for use in a patient. FIG. 16 illustrates an example of an appliance 100 fabricated using one or more of the digital models described herein. Certain example fabrication processes are described below. However, one of skill in the art will appreciate that any suitable fabrication process may be used to manufacture appliances (or components thereof) as disclosed herein.

In some embodiments, an orthodontic appliance 100 can be fabricated using a planar digital appliance model (e.g., the planar appliance digital model 1500). For example, the planar appliance digital model can include planar or substantially 2D shape data. The planar shape data can be provided to a suitable fabrication device (such as, but not limited to one or more machines that perform cutting, laser cutting, milling, chemical etching, wire electrical discharge machining (EDM), water jetting, punching (stamping), etc.) for cutting a flat sheet of material into a member having a shape corresponding to the planar appliance digital model 1500. The member may be cut from a flat sheet of any suitable material, such as, but not limited to Nitinol, stainless steel, cobalt chrome, or another type of metal, a polymer, a superelastic material, etc. The sheet of material can have a thickness selected to achieve the desired material properties of the resulting member. In various embodiments, the thickness of the sheet of material can be uniform or can vary (e.g., along a gradient, being thinned at particular regions using etching, grinding, etc., or thickened at particular regions using deposition, etc.). In some examples, the sheet can have a thickness of between about 0.1 mm and about 1.0 mm, between about 0.2 mm and about 0.9 mm, between about 0.3 mm and about 0.8 mm, between about 0.4 mm and about 0.7 mm, or about 0.5 mm. In some embodiments, the sheet can have a thickness of less than about 1.5 mm, less than about 1.4 mm, less than about 1.3 mm, less than about 1.2 mm, less than about 1.1 mm, less than about 1.0 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm.

Next, the cut member can be bent from its substantially planar form into a contoured arrangement. FIG. 16 illustrates an example of a completed appliance 100 resulting from such bending of a planar member. As illustrated, and as described elsewhere herein, the appliance 100 can include an anchor 120 and a plurality of arms 130 extending away from the anchor 120. Each arm 130 can include an attachment portion 40 configured to mate with a securing member adhered to a patient's tooth, and a biasing portion 150 disposed between the attachment portion 40 and the anchor 120. When the appliance 100 is installed in the patient's mouth, each of the arms 130 can connect to a different one of the teeth to be moved and exerts a specific force on its respective tooth, thereby allowing an operator to move each tooth independently.

In some embodiments, the planar member, after being cut from a sheet or otherwise formed, may be bent or otherwise manipulated into a shape or contour corresponding or substantially corresponding to the FTA configuration. For example, the member can be a shape cut from a flat sheet of Nitinol or other suitable material and assume a generally planar configuration. The member can be bent into a desired 3D or contoured configuration, for example corresponding to the contoured appliance digital model 1600. In certain examples, one or more fixtures are configured for use in bending the planar member into the desired 3D shape. In such examples, after cutting the planar member, the planar member can be fixed on or between one or more fixtures and bent or otherwise manipulated to form a desired 3D shape. In some embodiments, either before or after cutting the member from the sheet, the thickness of the member can be modified at least in some portions to achieve desired material properties. For example, the thickness of the member can be reduced in at least some regions using grinding, chemical etching, photoetching, electrical discharge machining, or any other suitable material removal process. The thickness of the member can be increased in at least some regions using thin film deposition, electroplating, or any other suitable additive technique. In some embodiments, the planar member can be formed using 3D printing or other technique instead of or in addition to cutting the planar member from a sheet of material. 3D printing may provide certain advantages, for example ease of controlling the thickness of different portions of the appliance. In some embodiments, the planar member can be formed by 3D printing metal, a polymer, or any other suitable material amendable to additive manufacturing by 3D printing.

In some embodiments, the appliance can be shape set into the desired contoured or 3D configuration (e.g., corresponding to the FTA). One or more shape setting procedures, such as, but not limited to heat treatment, may be applied to the appliance while held in the desired 3D shape, during or after the bending operation, to set the desired 3D shape. A shape setting procedure involving a heat treatment may include rapid cooling, following heating of the member during or after bending. Additional details regarding example heat treatment and associated fixtures are described below.

By employing a cut planar member, instead of a traditional single-diameter wire, a greater variety of resulting 3D shapes may be made, as compared to shapes made by bending single-diameter wire. The cut planar member may have designed or varying widths and lengths that, when bent into a desired shape, can result in portions of the 3D appliance having variances in thickness, width and length dimensions. In this manner, the planar member can be cut into a shape that provides a desired thickness, width and length of biasing portions, arms, or other components of the appliance. A larger variety of shapes may be provided by bending a custom cut planar member, as compared to bending a single-diameter wire.

In some examples, the entire appliance (including arms and anchor) is fabricated by bending the cut planar member into the desired 3D shaped member. In other examples, additional components may be attached to the 3D shape, for example, after bending. Such additional components may include, but are not limited to attachment portions 40, biasing portions 150, arms 130, etc. Such additional components may be attached to the 3D shaped member by any suitable attachment mechanism including, but not limited to, adhesive material, welding, friction fitting, etc.

In some embodiments, the appliance can be 3D printed directly into the desired contoured or 3D shaped configuration. In some embodiments, the 3D shaped member can be 3D printed, for example using any suitable material. In cases in which the appliance is 3D printed using Nitinol, there may be no need for a shape-setting process (e.g., heat treatment). Additionally, 3D printing may allow the use of different geometries (e.g., a cross-sectional shape of the anchor member may be oval, rather than rectangular, which may increase patient comfort on both the gingival-facing and lingual-facing sides of the anchor).

Methods of Shape-Setting Orthodontic Appliances

As noted previously, in some embodiments a heat treatment fixture model (e.g., the heat treatment fixture model 1200 (FIG. 12)) can be used to generate an appliance digital model. For example, the planar appliance digital model 1500 can be obtained based at least in part on the heat treatment fixture model 1200. The heat treatment fixture model 1200 may also be used to manufacture a heat treatment fixture, which is then used to shape-set the appliance (e.g., a planar member cut from a sheet of material can be formed into the desired 3D shape by use of the heat treatment fixture).

Figure 17:
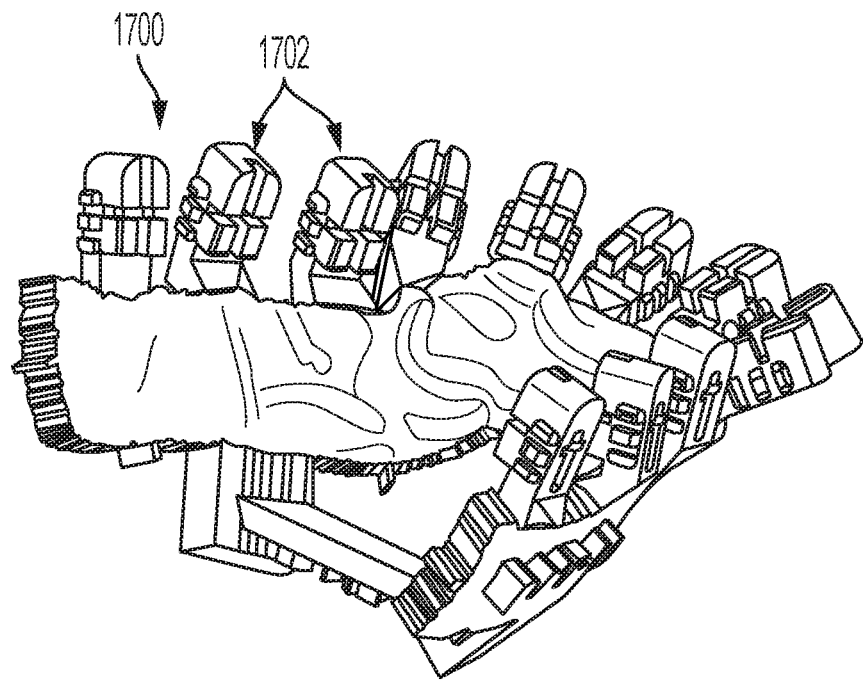
FIG. 17 illustrates a perspective view off a heat treatment fixture for an appliance in accordance with the present technology.

FIG. 17 illustrates an example of a heat treatment fixture 1700. The fixture 1700 can be manufactured based on the heat treatment fixture digital model (e.g., the fixture digital model 1200 (FIG. 12)). For example, the digital model or associated data can be provided to a fabricating system to produce a physical model based on the fixture model. In one example, the fixture data can be used to 3D print a model of the fixture in wax. The wax model may then be used to investment cast the fixture in brass or other suitable material. In some embodiments, the fixture can be 3D printed directly in brass or other suitable material (e.g., stainless steel, bronze, a ceramic or other material that tolerates high temperatures required for heat treatment). As shown in FIG. 17, the fixture 1700 can include securing portions 1702 configured to mate with attachment portions 40 of an appliance 100.

Figure 18:
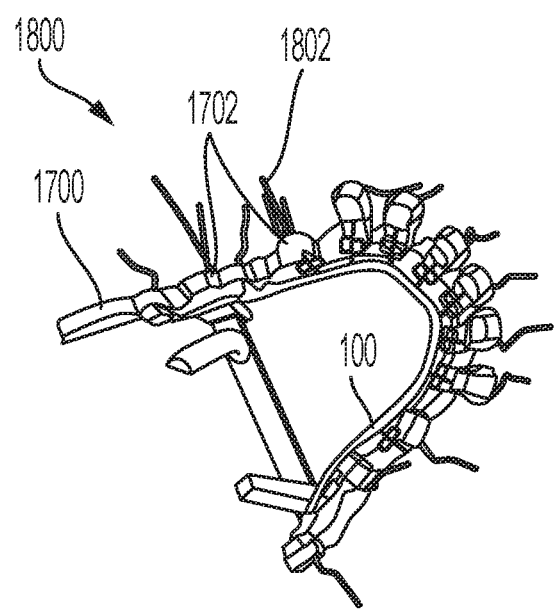
FIG. 18 is a perspective view of an orthodontic appliance fastened to a heat treatment fixture in accordance with the present technology.

In some embodiments, the fabricated fixture may be used to heat set an appliance. For example, as shown in FIG. 18, a combined assembly 1800 can include an appliance 100 that has been bent or otherwise manipulated into shape against a surface of the heat treatment fixture 1700. The appliance 100 can be coupled to the fixture 1700 by placing attachment portions of the arms into the securing portions 1702 of the fixture. Ligature wires 1802 or other suitable fasteners can be wrapped around the appliance 100 at a plurality of positions to secure the appliance 100 with respect to the fixture 1700. Next, heat can be applied to heat set the appliance 100, after which the appliance 100 can be removed from the fixture 1700.

One example, of a heat treatment procedure can include heating the appliance 100 to a selected temperature (such as, but not limited to 525 degrees centigrade) for a selected period of time (such as, but not limited to 20 minutes), followed by rapid cooling. The rapid cooling can be achieved by any suitable cooling procedure such as, but not limited to water quench or air-cooling. In other examples, the time and temperature for heat treatment can be different than those discussed above, for example, based upon the specific treatment plan. For example, heat treatment temperatures can be within a range from 200 degrees centigrade to 700 degrees centigrade and the time of heat treatment can be a time in the range up to about one hundred and twenty minutes. In particular examples, the heat treatment procedure may be carried out in an air or vacuum furnace, salt bath, fluidized sand bed or other suitable system. After completing the heat treatment, the appliance has a desired 3D shape and configuration (e.g., corresponding substantially to the heat treatment fixture and/or to the desired FTA). In other examples, other suitable heat-treating procedures may be employed including, but not limited to resistive heating or heating by running a current though the metal of the appliance structure.

One or more additional post processing operations may be provided on the 3D shaped article, including, but not limited to abrasive grit blasting, shot peening, polishing, chemical etching, electropolishing, electroplating, coating, ultrasonic cleansing, sterilizing or other cleaning or decontamination procedures.

In examples in which the appliance is made of multiple components, some (or each) of the components of the appliance may be made according to methods described above, and then connected together to form the desired 3D appliance configuration. In these or other examples, the appliance (or some or each component of the appliance) may be made in other suitable methods including, but not limited to: directly printing of metal, first printing of a wax member and then investment casting the wax member into a metal or other material, printing of elastomeric material or other polymer, cutting or machining out of solid material, or cutting the components out of a sheet of metal and shape setting into the desired 3D configuration.

As discussed herein, one or more heat treatment fixtures may be configured for use in bending a cut planar member into a desired 3D shape configuration. In particular examples, one or more heat treatment fixture is provided (such as, but not limited to, custom made) for each jaw of a patient. For example, the heat treatment fixtures may be customized in shape and configuration for each patient and can be made in any suitable manner, including molding, machining, direct metal printing of stainless steel or other suitable metals, 3D printing of a suitable material, such as, but not limited to stainless steel via powder bed fusion, or a steel/copper mix via binder jetting, as well as first printing the configuration in wax and then investment casting the wax into various metals. In various examples described herein, the heat treatment fixtures may be configured of material that is sufficiently resistant to the temperature of the heat treatment. In particular examples, one or more robots may be employed with or without the one or more heat treatment fixtures, for bending the cut planar member into a desired 3D shape configuration.

In some embodiments, a single shape-setting step may be completed to deform the member from its planar configuration to its desired 3D configuration. However, in certain embodiments the shape setting may include two or more shape-setting steps (e.g., two or more heat treatment processes, potentially using two or more different heat treatment fixtures). In such cases, the amount of deformation imparted to the appliance within each shape-setting step may be limited, with each subsequent shape-setting step moving the appliance further toward the desired 3D configuration.

The completed appliances can then be sent (optionally along with bonding trays and/or securing members) to the treating clinician. To install the appliances, the orthodontist can clean the lingual side of the patient's teeth to prepare them for bonding (e.g., with pumice powder). The surface of the teeth can then be sandblasted (e.g., with 50-micron aluminum oxide). The securing members can then be attached using a bonding tray as described elsewhere herein.

After the appliances are fabricated and the securing members are attached to the teeth, each arm can be coupled to its corresponding securing member element to install the appliance. Once installed, the appliance imparts forces and torques on the teeth, to move the teeth to the desired FTA. After treatment is completed (e.g., OTA to FTA, OTA to ITA, ITA to ITA, or ITA to FTA) the arms may sit passively in the securing members and force will no longer be applied to the teeth. Alternatively, any remaining force applied by the arms may fall below a threshold for causing further displacement of the teeth.

The patient can return for a check-up appointment (e.g., at approximately 2-3 months), and if the treatment is advancing as planned, nothing is done until the patient returns at a planned time for appliance removal. At this stage the securing members may be removed. If treatment is not progressing as planned, the appliance may be removed, the patient's mouth rescanned, and a new appliance can be device designed and installed based on a modified treatment plan.

CONCLUSION

Although many of the embodiments are described above primarily with respect to systems, devices, and methods for orthodontic appliances positioned on a lingual side of a patient's teeth, the technology is applicable to other applications and/or other approaches, such as orthodontic appliances positioned on a facial side of the patient's teeth. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-18.

The descriptions of embodiments of the technology are not intended to be exhaustive or to limit the technology to the precise form disclosed above. Where the context permits, singular or plural terms may also include the plural or singular term, respectively. For example, embodiments described herein as using multiple coupling arms may just as well be modified to include fewer (e.g., one) or more (e.g., three) coupling arms. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A method comprising:
   receiving data representing a patient's anatomical gingiva and teeth in a first tooth arrangement;
   creating a first digital model representing the patient's anatomical gingiva and teeth in a second tooth arrangement;
   creating a second digital model of a shaping fixture forming a shape of an orthodontic appliance for moving a patient's teeth from the first tooth arrangement to the second tooth arrangement, wherein the second digital model is based on the data and the first digital model, the second digital model comprising (a) a gingiva portion characterizing a thickened version of the patient's anatomical gingiva, and (b) securing portions characterizing positions of the patient's teeth in the second tooth arrangement, each of the securing portions defining a vertical channel;
   fabricating a physical shaping fixture based on the second digital model of the shaping fixture; and
   releasably securing a first portion of the orthodontic appliance against the gingiva portion of the physical shaping fixture and second portions of the orthodontic appliance within corresponding vertical channels in the securing portions of the physical shaping fixture, wherein the orthodontic appliance is secured such that the orthodontic appliance has a shape based at least in part on a shape of the physical shaping fixture and the first portion of the orthodontic appliance conforms to the gingiva portion such that, when the orthodontic appliance is secured to the patient's teeth, the first portion of the appliance does not impinge the patient's anatomical gingiva.

2. The method of claim 1, further comprising generating a digital model of the orthodontic appliance, wherein the digital model of the orthodontic appliance has a shape based at least in part on the second digital model of the shaping fixture.

3. The method of claim 1, further comprising generating a digital model of the orthodontic appliance by positioning a portion of the digital model of the orthodontic appliance at or adjacent to the gingiva portion of the second digital model of the shaping fixture.

4. The method of claim 1, wherein fabricating the physical shaping fixture comprises one or more of molding, 3D-printing, or casting.

5. The method of claim 1, wherein the orthodontic appliance is in an intermediate form prior to being secured to the physical shaping fixture, and wherein securing the intermediate form to the physical shaping fixture changes a shape of the intermediate form to reflect a treatment form of the orthodontic appliance.

6. The method of claim 5, further comprising shape setting the intermediate form of the orthodontic appliance in the shape of the treatment form by applying a heat treatment to the intermediate form while the intermediate form is secured to the physical shaping fixture.

7. The method of claim 1, wherein receiving the data includes obtaining digital image data of the patient's upper and/or lower jaw.

8. The method of claim 1, wherein a lingual surface of the gingiva portion of the second digital model is moved lingually relative to a lingual surface of the patient's anatomical gingiva in the first digital model.

9. The method of claim 8, wherein the lingual surface of the gingiva portion is moved lingually relative to lingual surface of the patient's anatomical gingiva by less than about 1.5 mm.

10. The method of claim 8, wherein the lingual surface of the gingiva portion is moved lingually relative to lingual surface of the patient's anatomical gingiva by less than about 0.5 mm.

11. A method comprising:
    obtaining first data corresponding to a first three-dimensional shape of a patient's jaw, wherein the first data includes a digital original tooth arrangement (OTA) of a patient's teeth and gingiva;
    obtaining second data corresponding to a second three-dimensional shape of the patient's jaw, wherein the second data includes a digital intermediate tooth arrangement (ITA) or a digital desired final tooth arrangement (FTA) of the patient's teeth and gingiva;
    obtaining a digital model of a shaping fixture configured to retain an orthodontic appliance in a particular configuration during a shape setting process, the shaping fixture being custom made for a particular patient based at least in part on the first and second data, wherein the shaping fixture digital model comprises (a) a gingiva portion characterizing a thickened version of the patient's gingiva and (b) a plurality of securing portions, each defining a through-channel and having positions based at least in part on positions of the patient's teeth in the ITA or the FTA, wherein the securing portions are configured to engage one or more portions of the orthodontic appliance such that the one or more portions of the orthodontic appliance are located at positions based at least in part on the positions of the patient's teeth in the ITA or the FTA; and
    obtaining a physical shaping fixture based on the shaping fixture digital model.

12. The method of claim 11, further comprising:
    obtaining a planar form of the orthodontic appliance, the planar form comprising an anchor configured to be disposed adjacent the patient's teeth and a plurality of arms extending from first ends at the anchor to second ends away from the anchor; and
    securing the second ends of the arms to the securing portions of the shaping fixture such that the orthodontic appliance is in a treatment form and substantially conforms to the shaping fixture.

13. The method of claim 12, further comprising setting a shape of the orthodontic appliance in the treatment form, while the second ends of the arms of the orthodontic appliance are secured to the securing portions of the shaping fixture.

14. The method of claim 13 wherein, after setting the shape of the appliance with the second ends of the arms secured to the securing portions, the second ends of the arms are configured to be secured to the patient's teeth such that the anchor is spaced apart from the patient's gingiva.

15. The method of claim 14, wherein the second ends of the arms are configured to be secured to the patient's teeth such that the anchor is spaced apart from the patient's gingiva by less than about 1.5 mm.

16. The method of claim 14, wherein the second ends of the arms are configured to be secured to the patient's teeth such that the anchor is spaced apart from the patient's gingiva by less than about 0.5 mm.

17. The method of claim 12, wherein, when the second ends of the arms are engaged with the securing portions, the anchor substantially conforms to the gingiva portion of the shaping fixture.

18. The method of claim 11, wherein the gingiva portion has a contour substantially corresponding to a contour of the thickened version of the patient's gingiva.

19. The method of claim 11, wherein, when the securing portions engage the one or more portions of the orthodontic appliance, the securing portions prevent mesiodistal movement of the one or more portions of the appliance.

20. The method of claim 11, wherein each securing portion comprises a plurality of protrusions including a first protrusion, a second protrusion, and a third protrusion, the plurality of protrusions defining a channel for receiving the one or more portions of the orthodontic appliance therein, and wherein the first protrusion is substantially mesiodistally aligned with and occlusogingivally offset from the second protrusion and the second protrusion is occlusogingivally aligned with and mesiodistally offset from the third protrusion.

* * * * *

UNITED STATES PATENT AND TRADEMARK OFFICE
CERTIFICATE OF CORRECTION

PATENT NO. : 12,295,808 B2
APPLICATION NO. : 15/929442
DATED : May 13, 2025
INVENTOR(S) : Roein Peikar et al.

Page 1 of 1

It is certified that error appears in the above-identified patent and that said Letters Patent is hereby corrected as shown below:

In the Claims

In Column 39, in Claim 1, Line 8, after "fixture" insert -- for --.

In Column 40, in Claim 14, Line 55, after "claim 13" insert -- , --.

Signed and Sealed this
Twenty-ninth Day of July, 2025

Coke Morgan Stewart
*Acting Director of the United States Patent and Trademark Office*